United States Patent [19]

Zenitz

[11] 4,069,256
[45] Jan. 17, 1978

[54] ANTI-INFLAMMATORY PHENYL-LOWER-ALKYLAMINES

[75] Inventor: Bernard L. Zenitz, Colonie, N.Y.

[73] Assignee: Sterling Drug Inc., New York, N.Y.

[21] Appl. No.: 641,511

[22] Filed: Dec. 17, 1975

Related U.S. Application Data

[63] Continuation-in-part of Ser. No. 542,553, Jan. 20, 1973, abandoned.

[51] Int. Cl.² ............................................. C07C 87/28
[52] U.S. Cl. ........................... 260/570 R; 260/268 R; 260/268 C; 260/293.55; 260/293.78; 260/293.87; 260/326.13 R; 260/442; 260/456 P; 260/501.18; 260/501.19; 260/566 A; 260/599; 424/248.57; 424/250; 424/267; 424/274; 424/316; 424/330; 544/3; 544/63
[58] Field of Search ........... 260/570 R, 501.18, 501.19

[56] References Cited

U.S. PATENT DOCUMENTS

| 2,827,460 | 3/1958 | Stein et al. | 260/570 X |
| 2,894,033 | 7/1959 | Jansson et al. | 260/570 X |
| 2,989,533 | 6/1961 | Stein et al. | 260/570 X |

OTHER PUBLICATIONS

Burger, "Medicinal Chemistry", 2nd Ed., pp. 82–83, (1960).

*Primary Examiner*—Robert V. Hines
*Attorney, Agent, or Firm*—William G. Webb; B. Woodrow Wyatt

[57] ABSTRACT

N-{3-[$R_1$-(phenyl)-C(=X)]-phenyl-lower-alkyl}amines having anti-inflammatory utility are prepared either by reduction of a 3-[$R_1$-(phenyl)-CO]-phenyl-lower-alkanoylamine; by benzoylating a phenyl-lower-alkylamine; by reaction of a 3-lithiophenyl-lower-alkylamine with a $R_1$-(phenyl)-carboxaldehyde, a $R_1$-(phenyl)lower-alkyl ketone or a $R_1$-(phenyl)-carbonitrile or by transformations involving manipulations of a carbonyl or carbinol group.

4 Claims, No Drawings

ANTI-INFLAMMATORY PHENYL-LOWER-ALKYLAMINES

RELATED APPLICATIONS

This is a continuous-in-part of my prior, copending application Ser. No. 542,553, filed Jan. 20, 1975, now abandoned.

BACKGROUND OF THE INVENTION a. Field of the Invention

This invention relates to N-{3-[$R_1$-(phenyl)-C(=X)]-phenyl-lower-alkyl} amines useful as anti-inflammatory agents.

b. Description of the Prior Art

A very large class of organic compounds of widely diverse structural types are known to be useful as anti-inflammatory agents, but many of such anti-inflammatory agents are acidic, for example α-(3-benzoylphenyl)propionic acid, known generically as ketoprofen (British Pat. No. 1,164,585, published Sept. 17, 1969). Such acidic agents are often irritating, and in some cases are ulcerogenic, so the gastric mucosa when administered orally. There is thus a great need for anti-inflammatory agents, for example compounds having a basic amine function, which might be expected to be non-irritating to the gastric mucosa. Although the chemical literature describes numerous types of amine-substituted compounds asserted to have anti-inflammatory activity [see for example U.S. Pat. Nos. 3,770,748, patented Nov. 6, 1973 and 3,803,127, patented Apr. 9, 1974 (N-phenylpolymethyleneimines); U.S. Pat. Nos. 3,772,311, patented Nov. 13, 1973 and 3,773,772, patented Nov. 20, 1973 (polymethyleneimino-lower-alkanoylpyrazoles); U.S. Pat. No. 3,773,944, patented Nov. 20, 1973 (1-[3-aminopropyl]phthalans); U.S. Pat. No. 3,801,594, patented Apr. 2, 1974 (3-amino-loweralkylindoles); U.S. Pat. No. 3,810,985, patented May 14, 1974 (4-anilino-1,3,5-triazines) and French Pat. No. 1,549,342, delivre Nov. 4, 1968, (4-[benzoylphenylmethyl]morpholines)], no such basic compounds are known to be commercially available, and none are known to be under advanced investigation by pharmacologists for possible commercial development. The search for an effective, non-acidic anti-inflammatory agent for commercial development has therefore continued.

SUMMARY OF THE INVENTION

In one of its composition of matter aspects, the invention relates to certain N-{3-[$R_1$-(phenyl)-C(=X)]-phenyl-lower-alkyl}amines:

which are useful as anti-inflammatory agents.

In a second composition of matter aspect, the invention relates to certain N-{3-[$R_1$-(phenyl)-C(=X)]-phenyl-lower-alkanoyl}amines:

3-[$R_1$-(phenyl)-C(=X)]-phenyl-CHR$_3$CO-N=B which are useful as intermediates for the preparation of the final products.

In one of its process aspects, the invention relates to a process for preparing certain amino-carbinols of the invention:

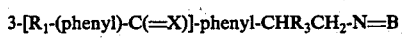

comprising reducing a corresponding keto-amide:

3-[$R_1$-(phenyl)-CO]-phenyl-CHR$_3$CO-N=B with reagents effective to reduce amides to amines, for example an alkaline metal aluminum hydride, a trialkylaluminum or a dialkylaluminum hydride.

In a second process aspect, the invention relates to a process for preparing certain keto-amines of the invention:

comprising oxidizing a corresponding amino-carbinol:

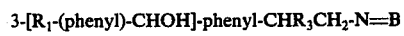

with chromic acid or with a nitric acid/perchloric acid mixture.

In a third process aspect, the invention relates to a process for preparing certain keto-amines of the invention:

3-[$R_1$-(phenyl)-CO]-4-$R_3$O-phenyl-CHR$_3$CH$_2$-N=B comprisng reacting certain phenyl-lower-alkylamines:

4-$R_3$O-phenyl-CHR$_3$CH$_2$-N=B with certain benzoic acid halides:

in the presence of a Lewis acid.

In a fourth process aspect, the invention relates to a process for preparing certain amino-carbinols:

comprising reacting certain 3-lithio phenyl-lower-alkylamines:

3-Li-phenyl-CHR$_3$CH$_2$-N=B with a $R_1$-benzaldehyde:

$R_1$-(phenyl)-CHO.

In a fifth process aspect, the invention relates to a process for preparing certain keto-amines of the invention:

comprising reacting certain 3-lithio phenyl-lower-alkylamines:

3-Li-phenyl-CHR$_3$CH$_2$-N=B with a $R_1$-benzonitrile:

$R_1$-(phenyl)-CN.

In a sixth process aspect, the invention relates to a process for preparing certain 3-benzylphenyl-lower-alkylamines of the invention:

3-[$R_1$-(phenyl)-C($R_3$)H]-phenyl-CHR$_3$CH$_2$-N=B comprising reducing with hydrogen in an acid medium a corresponding amino-carbinol:

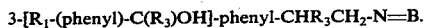

In a seventh process aspect, the invention relates to a process for preparing an oximine of certain keto-amines of the invention:

which comprises reacting a corresponding keto-amine:

with hydroxylamine.

In an eighth process aspect, the invention relates to a process for preparing certain amino-amines of the invention:

3-[$R_1$-(phenyl)-CHNH$_2$]-phenyl-CHR$_3$CH$_2$-N=B which comprises reducing with sodium in a lower-alkanol an oximine of a corresponding keto-amine:

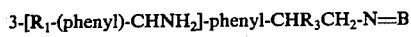

In a ninth process aspect, the invention relates to a process for preparing certain 3-(1-phenyl-1-vinyl)phenyl-lower alkylamines of the invention:

which comprises reacting with concentrated sulfuric acid a corresponding amino-carbinol:

3-[$R_1$-(phenyl)-C(CH$_3$)OH]-phenyl-CHR$_3$CH$_2$-N=B.

In a tenth process aspect, the invention relates to a process for preparing certain dimethylamino-amines of the invention:

3-[$R_1$-(phenyl)-CHN(CH$_3$)$_2$]-phenyl-CHR$_3$CH$_2$-N=B which comprises reacting a corresponding primary amino-amine:

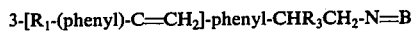

with formaldehyde in the presence of formic acid.

In an eleventh process aspect, the invention relates to a process for preparing certain 3-benzoylphenyl-lower-alkylamines of the invention:

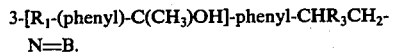

which comprises reacting a 3-benzoylphenyl-lower-alkyl p-toluenesulfonate:

3-[$R_1$-(phenyl)-CO]-phenyl-CHR$_3$CH$_2$OTs with amine, H—N=B, in the presence of an acid-acceptor.

DETAILED DESCRIPTION INCLUSIVE OF THE PREFERRED EMBODIMENTS

More specifically, the invention relates to N-{3-[$R_1$-(phenyl)-C(=X)]-phenyl-lower-alkyl} amines, which are useful as anti-inflammatory agents, having the formula:

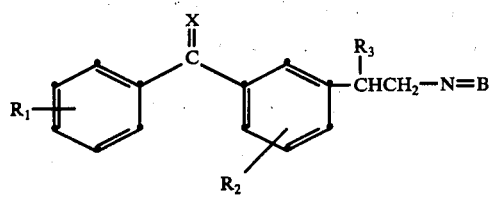

where $R_1$ represents hydrogen or from one or two, the same or different, lower-alkyl, hydroxy, lower-alkoxy, trifluoromethyl, lower-alkylmercapto, lower-alkylsulfinyl, lower-alkylsulfonyl or halogen selected from fluorine, chlorine and bromine; $R_2$ represents hydrogen, or lower-alkoxy or hydroxy in the 4-position, or lower-alkyl in either of the 2-, 4-, 5- or 6-positions; $R_3$ represents hydrogen or lower-alkyl; the group >C=X represents >C=O, >C($R_3$)OH, >C($R_3$)H, >C=CH$_2$, >C=NOH or >CHN($R_3$)$_2$; and N=B represents one of the groups.

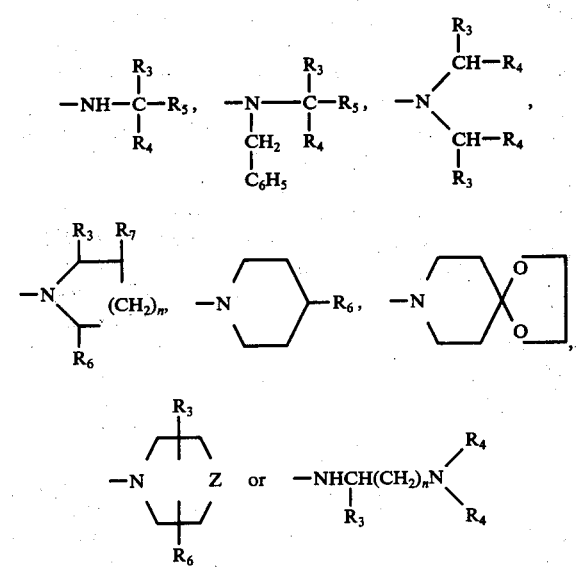

where $R_4$ and $R_5$ each represent lower-alkyl; $R_6$ and $R_7$ each represent hydrogen, lower-alkyl, cyclohexyl, cyclohexylmethyl, 2-cyclohexylethyl, 3-cyclohexylpropyl or benzyl; Z represents O, S or N-$R_8$; $R_8$ represents lower-alkyl or cyclohexyl; and n represents one of the integers 1, 2 and 3.

Preferred compounds of formula I are those where $R_1$ represents hydrogen of from one to two, the same or different, lower-alkyl, lower-alkoxy or halogen; $R_2$ represents hydrogen, or lower-alkoxy or hydroxy in the 4-position; and N=B represents one of the groups

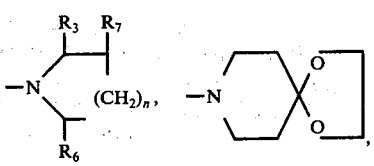

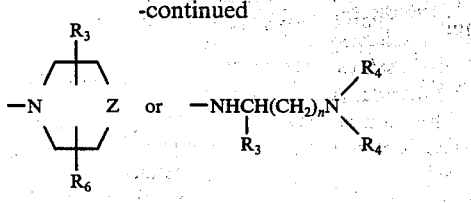 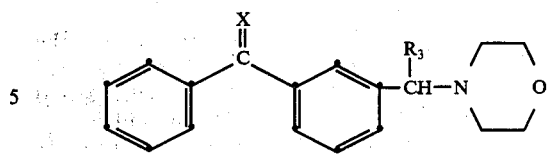

where the group $>C=X$ represents $>C=O$ and $R_3$ represents lower-alkyl or where the group $>C=X$ represents $>CHNH_2$ and $R_3$ represents hydrogen.

in which $R_6$ represents hydrogen, lower-alkyl, cyclohexyl, cyclohexylmethyl, 2-cyclohexylethyl or 3-cyclohexylpropyl; $R_7$ represents hydrogen; Z represents oxygen; and $R_3$, $R_4$ and $n$ have the meanings given above.

Particularly preferred compounds of formula I within the ambit of the invention as described above are those where $R_1$ represents hydrogen or from one to two, the same or different, lower-alkoxy or halogen; $R_2$ represents hydrogen; $>C=X$ represents $>C=O$, $>CHOH$, $>CH_2$, $>C=NOH$ or $>CHNH_2$; and $N=B$ represents one of the groups

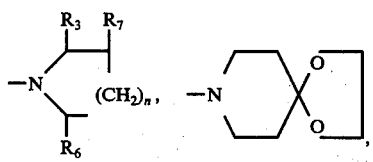

As used herein, the terms lower-alkyl and lower-alkoxy mean saturated, monovalent, aliphatic radicals, including branched chain radicals, of from one to four carbon atoms, for example methyl, ethyl, propyl, isopropyl, butyl, sec.-butyl, isobutyl, methoxy, ethoxy, propoxy, isopropoxy, butoxy, sec.-butoxy and isobutoxy.

The compounds of formula I in which the group $>C=X$ represents $>C(R_3)OH$ where $R_3$ is hydrogen are prepared by reaction of an appropriate 3-[$R_1$-(phenyl)-CO]-phenyl-lower-alkanoyl halide of formula III (prepared by reaction of the corresponding acid of formula II with a thionyl halide) with an appropriate amine of formula IV, H-N=B, and reduction of the resulting 3-[$R_1$-(phenyl)-CO]-phenyl-lower-alkanoylamine of formula V with a reagent effective to reduce amides to amines, for example an alkali metal aluminum hydride, a trialkylaluminum or a dialkylaluminum hydride. The method is represented by the following reaction sequence:

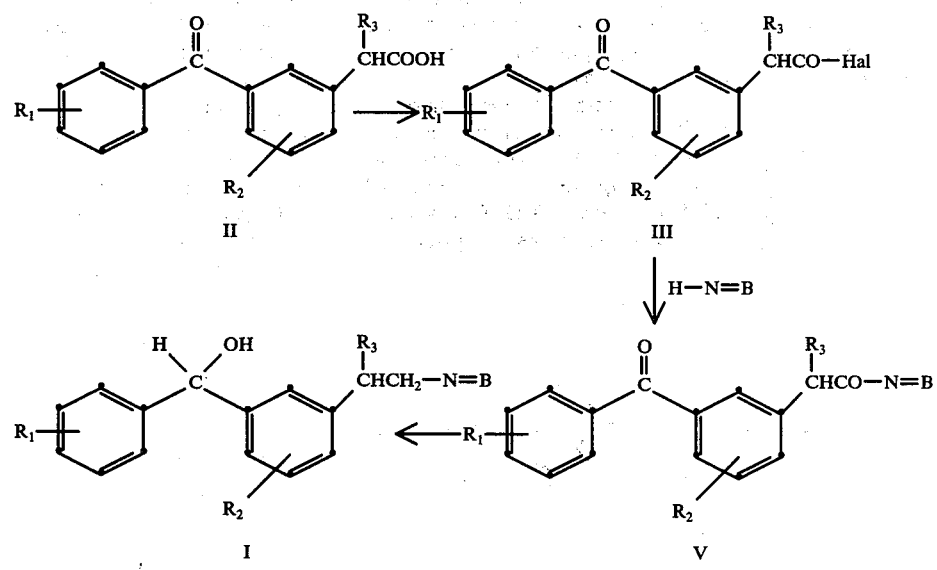

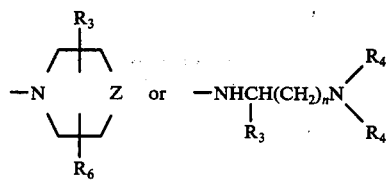

in which $R_6$ represents hydrogen, lower-alkyl, cyclohexyl, cyclohexylmethyl, 2-cyclohexylethyl or 3-cyclohexylpropyl; $R_7$ represents hydrogen; Z represents oxygen; n represents the integers 1 or 2; and $R_3$ and $R_4$ have the meanings given above.

Also within the purview of the present invention are compounds having the formula:

where $R_1$, $R_2$, $R_3$ and $N=B$ have the meanings given above, and Hal represents halogen. The preparation of the acid halide is carried out either with or without a solvent by heating the acid with a molar excess of the thionyl halide. Conversion of the halide to the amide of formula V is effected by reacting the halide with the amine in the presence of an acid-acceptor, for example an alkali metal carbonate or bicarbonate, a tri-lower-alkylamine or an excess of the amine, H-N=B. The reaction is preferably carried out in an inert organic solvent, for example methylene dichloride, benzene, toluene or xylene. Reduction of the amide with an alkali metal aluminum hydride is carried out in an inert organic solvent, for example diethyl ether, tetrahydrofuran, dioxane or dibutyl ether.

As indicated by the above reaction, reduction of the 3-[$R_1$-(phenyl)-CO]-phenyl-lower-alkanoylamines of formula V also effects reduction of the carbonyl group of the $R_1$-(phenyl)-CO moiety to the carbinol group, >CHOH. This reduction can be avoided if desired by protecting the carbonyl group of the $R_1$-(phenyl)-CO moiety with a ketal group, for example the ethylene glycol ketal. The ketals are prepared by reaction of the carbonyl compound with an alcohol in the presence of an acid catalyst under dehydrating conditions. The ketal group can then be removed by hydrolysis at a later stage after reduction of the amide function.

Alternatively, when the carbonyl group is reduced to the carbinol group, the carbinols can be reoxidized to the ketones if compounds where >C=X is a carbonyl group are desired. Preferred oxidizing agents for this purpose are chromic acid or nitric acid/perchloric acid, and it is preferred to carry out the reaction in an inert organic solvent, for example benzene when chromic acid is the oxidant and 1,2-dimethoxyethane when nitric acid/perchloric acid is the oxidant.

Another method for preparing the compounds of formula I, where >C=X is a carbonyl group and $R_2$ is hydroxy or lower-alkoxy in the 4-position, comprises acylating a phenyl-lower-alkylamine of formula VI with a benzoic acid halide for formula VII, $R_1$-(phenyl)-CO-Hal, under Friedel-Crafts conditions as represented by the reaction:

of formula VI to a stirred mixture of the acid chloride and a suitable Lewis acid which serves as a Friedel-Crafts catalyst, for example an aluminum halide or ferric chloride. A preferred catalyst is an aluminum halide.

The compounds of formula I where the group >C=X represents a carbonyl group can also be prepared by reaction of a 3-benzoylphenyl-lower-alkyl p-toluenesulfonate having the formula VIII with an amine, H-N=B, in the presence of an acid-acceptor according to the reaction:

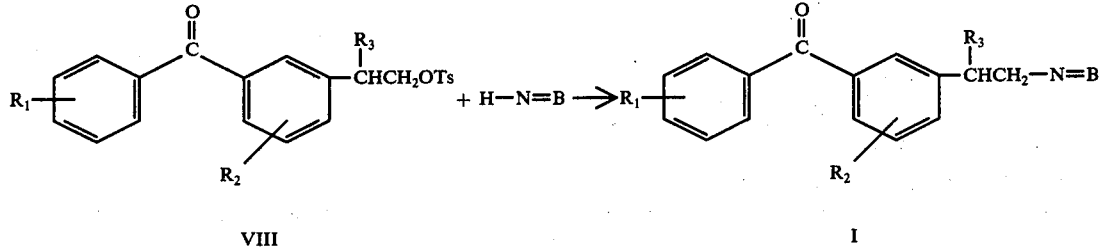

where $R_1$, $R_2$, $R_3$ and N=B have the meanings given above, and Ts represents the p-toluenesulfonyl group. The reaction is preferably carried out by heating the reactants in an inert organic solvent, for example dimethylformamide or a lower-alkanol. Suitable acid-acceptors are alkali metal carbonates or bicarbonates or an excess of the amine, H-N=B.

The tosylates of formula VIII are in turn prepared by a sequence of reactions involving reduction, with an alkali metal borohydride, of a 3-bromophenyl-lower-alkanaldehyde to the corresponding 3-bromophenyl-lower-alkanol; reaction of the latter with dihydropyran in the absence of solvent and in the presence of a few drops of concentrated hydrochloric acid to prepare the corresponding 3-bromophenyl-lower-alkane tetrahydropyranyl ether; reaction of the latter with butyl lithium followed by an appropriate $R_1$-(phenyl)-nitrile and hydrolysis of the tetrahydropyranyl ether group; and reaction of the resulting 3-benzoylphenyl-lower-alkanol with p-toluenesulfonyl chloride in the presence of pyri-

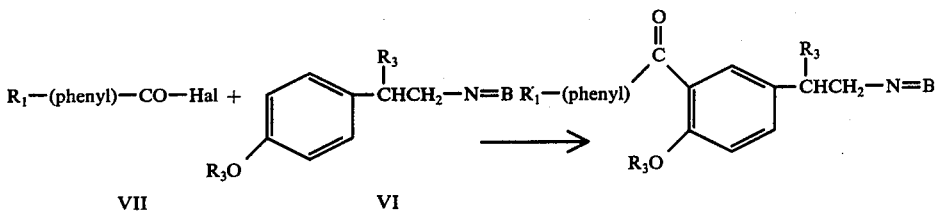

where $R_1$, $R_3$, N=B and Hal have the meanings given above. The reaction is carried out by adding the amine dine. The method is represented by the following reaction sequence:

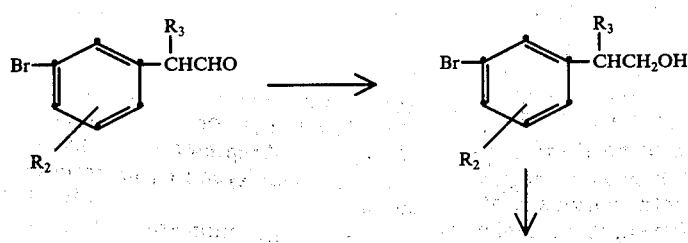

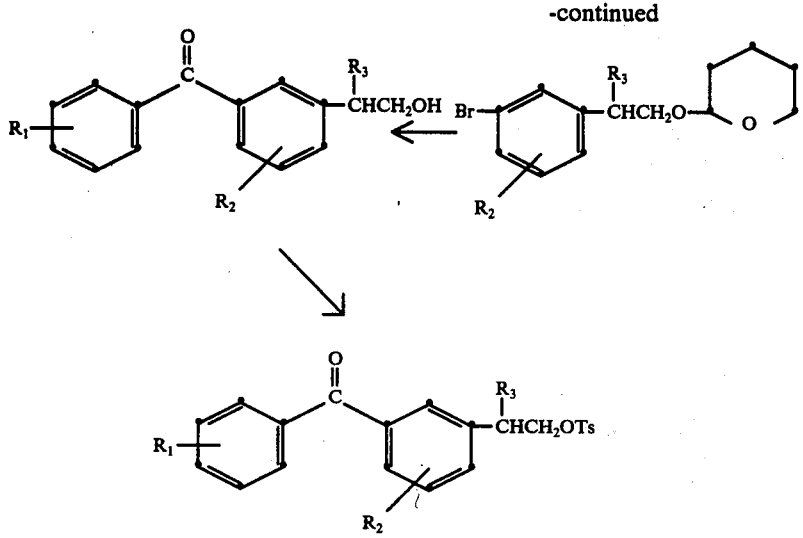

VIII where $R_1$, $R_2$ and $R_3$ have the meanings given above and Ts represents the p-toluenesulfonyl group.

The compounds of formula I where the group >C=X represents >C=O- or >C(R$_3$)OH where R$_3$ is hydrogen or lower-alkyl are prepared by reacting a 3-halophenyl-lower-alkylamine of formula IX with a lower-alkyl lithium in an aprotic organic solvent, for example diethyl ether, and reacting the resulting aryl lithium directly either with a R$_1$-(phenyl)-carbonitrile (to prepare the compounds where >C=X is >C=O) or with a R$_1$-(phenyl)-carboxaldehyde, R$_1$-(phenyl)-CHO, or (to prepare the compounds where R$_3$ is hydrogen), or with a R$_1$-(phenyl) lower-alkyl ketone, R$_1$-(phenyl)-COR$_3$ (to prepare the compounds where R$_3$ is lower-alkyl). During the course of the reaction of the aryl lithium with an aldehyde, and for reasons not completely understood, some of the carbinol product (C=X is CHOH) is oxidized to the ketone, and in such cases it is necessary to reduce the crude product with an alkali metal borohydride as described hereinbelow.

The 3-halophenyl-lower-alkylamines of formula IX are in turn prepared by one of two methods depending upon the identity of the group N=B in the final product. The compounds of formula IX where N=B is a secondary amino group are prepared by reaction of the corresponding primary amine with a 3-halophenyl-lower-alkanal of formula X, followed by reduction of the resulting Schiff base with an alkali metal borohydride. The compounds of formula IX where N=B is a tertiary amino group are prepared by reaction of a 3-halophenyl-lower-alkanal of formula X with a secondary amine, conversion of the resulting 3-halophenylvinylamine of formula XI to the iminium salt having the formula XII by reaction of the former with mineral acid, and reduction of the iminium salt with an alkali metal borohydride. The condensation of the aldehyde with the amine in the latter procedure is preferably carried out in a water immiscible solvent, for example benzene, toluene or xylene, at the reflux temperature thereof under a water separator which is used to collect the water as it is produced in the reaction. The reduction of the iminium salt with an alkali metal borohydride is carried out in an inert organic solvent, for example a lower-alkanol or dimethylformamide (DMF). The overall method is represented by the reaction sequence:

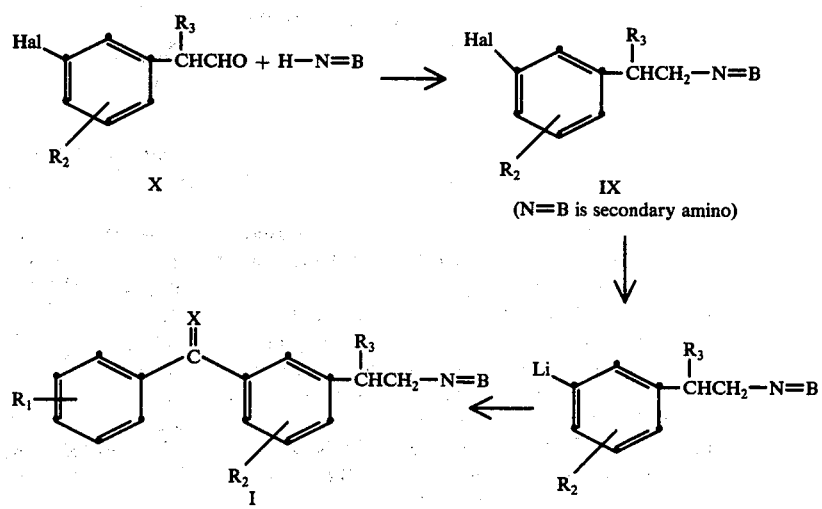

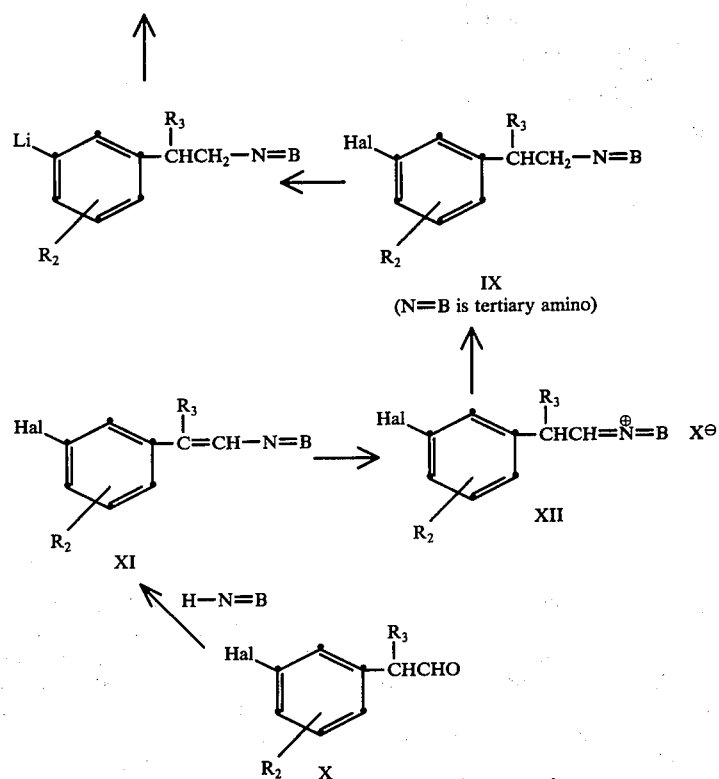

IX
(N=B is tertiary amino)

XII

XI where $R_1$, $R_2$, $R_3$, N=B and Hal have the meanings given above, and $X^-$ represents an anion of a mineral acid.

The methods described above are used to prepare the compounds of formula I where >C=X is either a carbonyl group, >C=O, or a carbinol group, >C(R₃)OH, where R₃ is either hydrogen or lower-alkyl. The compounds of formula I where the group >C=X has the other meanings given are prepared by simple chemical transformations involving the carbonyl or carbinol groups. Thus the compounds where the group >C=X represents >C(R₃)H, where R₃ is either hydrogen or lower-alkyl, are prepared by catalytic reduction with hydrogen of the corresponding carbinol, >C(R₃)OH, in the presence of perchloric acid. A preferred catalyst is palladium-on-charcoal, and it is preferred to carry out the reaction in glacial acetic acid as solvent. Reduction is carried out at a pressure in the range from 40–100 p.s.i.

The compounds of formula I where >C=X is the group >C=CH₂ are prepared by dehydration of the methyl carbinols, where >C=X is the group

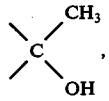

with concentrated sulfuric acid. The reaction is carried out by refluxing a solution of the carbinol and sulfuric acid in a lower-alkanol solvent.

The compounds of formula I where >C=X is the group >C=NOH are prepared from the corresponding ketones (>C=X is >C=O) by heating the latter with hydroxylamine in an inert organic solvent, for example a lower-alkanol.

The compounds of formula I where >C=X is the group CHNH₂ are preapared by reducing the corresponding oximes (>C=X is >C=NOH) with sodium in a lower-alkanol. The compounds of formula I where >C=X is >C=NOH, apart from their usefulness as pharmaceutically active compounds as described below, are thus also useful as intermediates for preparation of the compounds where >C=X is >CHNH₂.

The compounds of formula I in which >C=X represents >CHN(CH₃)₂ are prepared from the corresponding primary amines by treatment of the latter with formaldehyde in the presence of formic acid.

The compounds of formula Ia where >C=X represents >C=O are prepared by reaction of a 3-(phenyl-CO)-phenyl-CHR₃ halide of formula XIII with morpholine according to the reaction:

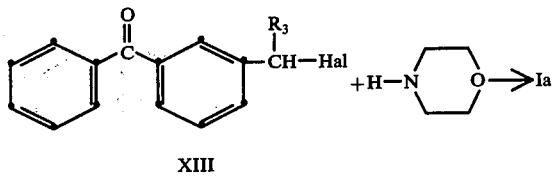

XIII where R₃ and Hal have the meanings given above. The reaction is carried out by reacting a solution of the halide with a molar excess of morpholine at ambient temperature in an inert organic solvent, for example methanol, ethanol, isopropanol or DMF. A preferred solvent is DMF.

The compounds of formula Ia where the group >C=X represents >CHNH₂ are prepared from the corresponding compounds where >C=X represents >C=O by conversion of the latter to the oxime and reduction of the latter to the amine as described above.

The amines of formula IV where -N=B is the group:

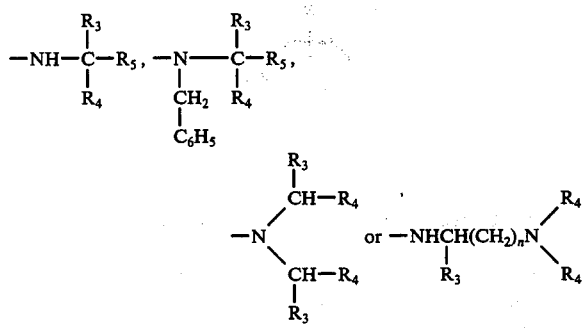

are known compounds.

The amines in which -N=B is the group:

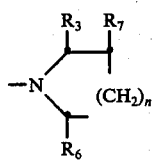

where n is 2 are also known, having been generally described in U.S. Pat. No. 3,238,215. As described therein, they are prepared by catalytic reduction over platinum oxide of appropriate $R_3$, $R_6$ or $R_7$-substituted pyridines, which are commercially available.

The amines where N=B is the group:

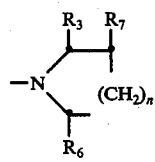

where n is the integer 1 and $R_7$ is hydrogen are prepared by refluxing a mixture of an appropriate alkanedione, ammonium acetate and glacial acetic acid, and catalytic reduction over platinum oxide of the resulting 2-$R_3$-5-$R_6$-pyrrole according to the reaction sequence:

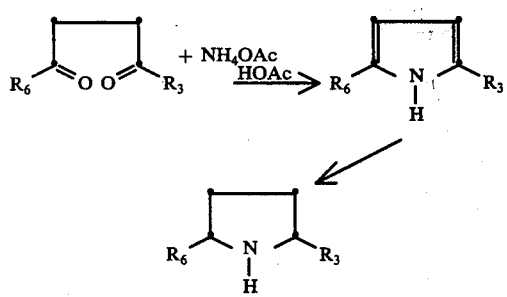

where $R_3$ and $R_6$ have the meanings given above.

Alternatively, the amines in which -N=B is the group:

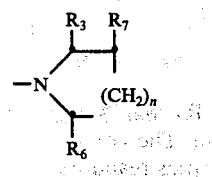

where n is 1 and $R_7$ is hydrogen are prepared by reaction of a Grignard reagent, $R_6$MgHal, with a 4-$R_3$-4-halobutyronitrile, $R_3$-CH-(Hal)-(CH$_2$)$_2$-CN; direct cyclization of the resulting 1-amino-1-$R_6$-4-$R_3$-4-halobutene; and catalytic reduction of the resulting 2-$R_6$-5-$R_3$-4,5-dihydropyrrole as indicated by the reaction sequence:

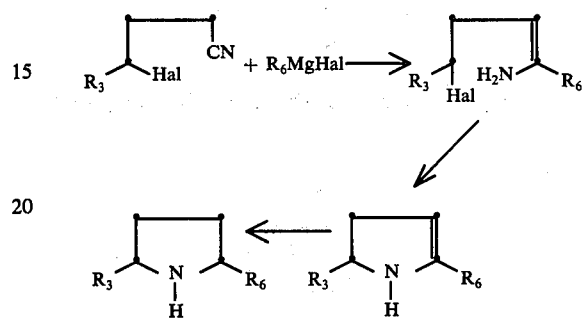

where $R_3$, $R_6$ and Hal have the meanings given above.

The amines where -N=B is the group:

are advantageously prepared, like the amines where -N=B is the group:

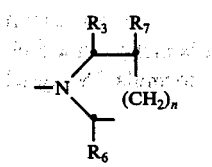

where n is 2, by catalytic reduction over platinum oxide of the corresponding 4-$R_6$-pyridine.

The amines where -N=B is the group:

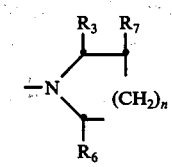

where $R_3$ and $R_7$ are hydrogen, n is the integer 3, and $R_6$ has the meanings given above are prepared by Beckmann rearrangement of an appropriate $R_6$-substituted-cyclohexanone oxime and reduction, with lithium aluminum hydride, of the resulting lactam according to the reaction:

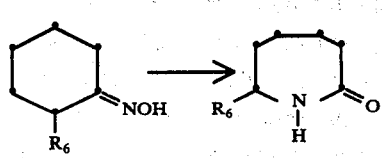

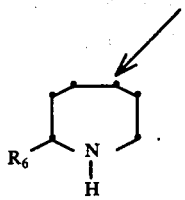

The amines of formula VI where -N=B is the group:

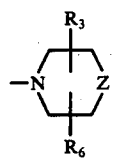

where Z is O are prepared according to the method described in British Pat. No. 835,717 which comprises passing a vaporized mixture of a glycol ether having the formula

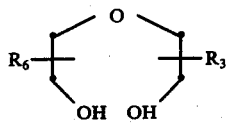

together with ammonia and hydrogen over a hydrogenation/dehydrogenation catalyst based on either nickel or cobalt at a temperature from 150° to 250° C. A preferred catalyst is nickel on kieselguhr.

The amines of formula IV in which -N=B is the group:

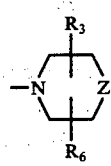

where Z is S are preferably prepared by the methods described by Idson et al., J. Am. Chem. Soc. 76, 2902 (1954) which involves either the reaction of sodium sulfide with an appropriate bis-2-haloethylamine:

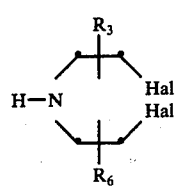

or the reaction of ammonia with an appropriate bis -2-haloethyl sulfide:

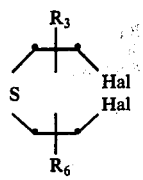

where $R_3$ and $R_6$ have the meanings given above, and Hal represents halogen.

The 3-[$R_1$-(phenyl)-CO]-phenyl-lower-alkanoic acids of formula II where $R_2$ is hydrogen or lower-alkyl are generally known compounds prepared by the methods described in British Pat. No. 1,164,585. Although the compounds of formula II where $R_2$ is hydroxy can also be prepared by the methods used to prepare the compounds where $R_2$ is hydrogen or lower-alkyl and the compounds of formula II so-prepared converted, as described above, to the final products of formula I, it is preferred to prepare the compounds of formula I where $R_2$ is hydroxy from a 4-lower-alkoxy-phenyl-lower-alkanoic acid by conversion of the latter to the corresponding acid halide; conversion of the latter to the corresponding 4-lower-alkoxyphenyl-lower-alkanoylamine by reaction of the acid halide with an amine, H-N=B, and reduction of the resulting amide with a reagent effective to reduce amides to amines, for example an alkali metal aluminum hydride; reaction of the resulting amine with an acid halide, $R_1$-(phenyl)-CO-Hal, using Friedel-Crafts conditions; and finally cleavage of the lower-alkoxy group to the hydroxy group, using well-known methods such as heating with hydrobromic acid. The method is represented by the following reaction sequence:

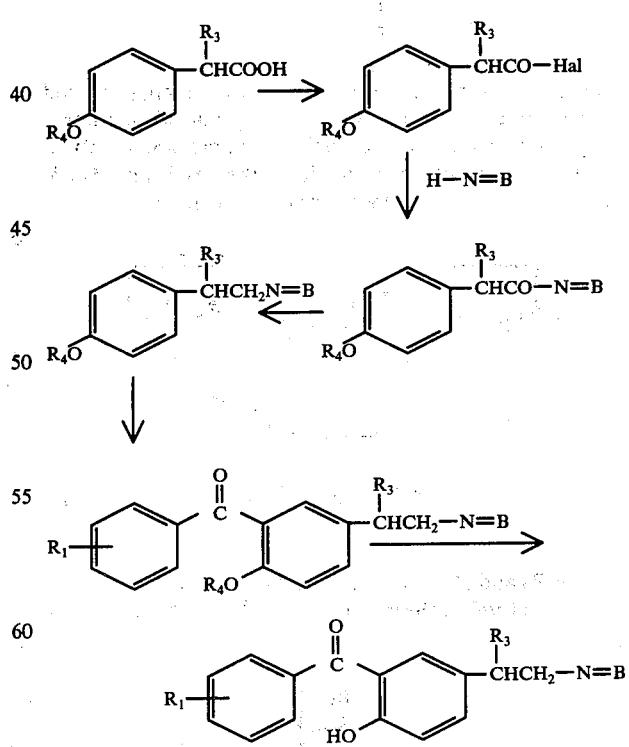

where $R_1$, $R_3$, $R_4$, N=B and Hal have the meanings given above. The reaction conditions for the first four reactions in this reaction sequence have been described above, and cleavage of the ether with hydrobromic acid is a conventional reaction well known to the organic chemist.

The 3-halophenyl-lower-alkanals of formula X are prepared via the Darzens glycidic ester condensation by reaction of a 3-halo-lower-alkanophenone with a lower-alkyl haloacetate in the presence of an alkali metal alkoxide and saponification and decarboxylation of the resulting glycidic ester. The method is represented by the following reaction sequence:

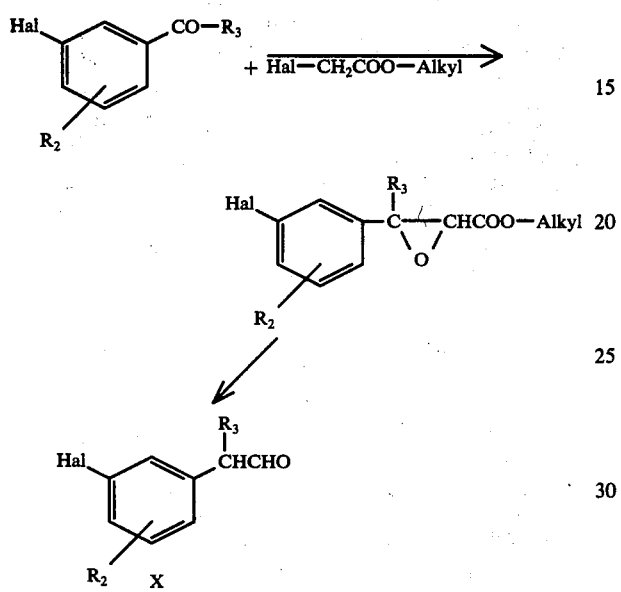

The novel compounds of the instant invention are the compounds of formulas I and Ia and the acid-addition salts thereof. The compounds of formulas I and Ia in free base form are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formulas I and Ia not only represent the structural configuration of the bases of formulas I and Ia but are also representative of the structural entities which are common to all of the compounds of formulas I and Ia, whether in the form of the free base or in the form of the acid-addition salts of the base. It has been found that by virtue of these common structural entities, the bases and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically-acceptable acids, that is acids whose anions are innocuous to the animal organism in effective doses of the salts so that beneficial properties inherent in the common structural entity represented by the free bases is not vitiated by side effects ascribable to the anions.

In utilizing this pharmacological activity of the salts of the invention, it is preferred, of course, to use pharmaceutically acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively they can be converted to any desired pharmaceutically-acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous base, or alternatively can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form and the like, and are accordingly within the purview of the instant invention.

The novel feature of the compounds of the invention, then, resides in the concept of the bases and cationic forms of the new N-{3-[R$_1$-(phenyl)-C(=X)]-phenyl-lower-alkyl}amines and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases. In fact, in aqueous solutions, the base form or water-soluble acid-addition salt form of the compounds of the invention both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and acid in an organic solvent and isolating the salt directly or by concentration of the solution.

Due to the presence of at least one and as many as four asymmetric centers in the compounds of the invention, i.e. the carbon atom adjacent the phenyl ring to which the group $R_3$ is attached and the various asymmetric centers in the group —N=B to which the groups $R_3$, $R_4$, $R_5$, $R_6$ and $R_7$ are attached, the compounds of the invention can exist in stereochemically isomeric forms which are all considered to be within the purview of the invention. If desired, the isolation or the production of a particular stereochemical form can be accomplished by application of general principles known in the art.

In standard pharmacological test procedures, the compounds of formulas I and Ia have been found to possess antiinflammatory activity and are useful as antiinflammatory agents. Certain compounds of formula I have also been found to have anti-viral activity and are thus also useful as anti-viral agents. Anti-inflammatory activity was determined using (1) the inhibition of carrageenin-induced foot edema test essentially described by Van Arman et al., Winter et al., Proc. Soc. Exp. Biol. and Med. III, 554 (1962) as modified by J. Pharmacol. Exptl. Therap. 150, 328 (1965) and (2) a modification of the inhibition of adjuvant-induced arthritis test described by Pierson, J. Chronic Diseases 16, 863 (1963) and Glenn et al., Am. J. Vet. Res. 26, 1180 (1965).

The in vitro anti-viral activity of the compounds against herpes simplex viruses types 1 and 2 was demonstrated by the addition of the compounds to tissue cultures infected with herpes virus. Monolayers of tissue cultures (BSC, cell line, monkey kidney) were infected with one hundred $TCID_{50}$ (Tissue Culture Infectious $Dose_{50}$) of infections virus. After one hour of virus absorption, fresh maintenance medium containing various concentrations of the test compound was added to the monolayers. Cultures were then incubated at 36°–37° C., and after 48 and 72 hours, cultures were examined microscopically. In the infected control tubes as well as in those containing inactive compounds, viral growth is indicated by the production of characteristic cytopathic effects with the destruction of the cells. In the presence of an active compound, cells grow normally similar to those in the tissue culture control. Simultaneously with the anti-viral evaluation, the toxicity of each compound was evaluated in separate cultures. Identical concentrations of the test compound were added to the tissue culture monolayers in the absence of virus. Those concentrations of the compound which show toxic effects on the cells were not considered in the anti-viral evaluation. The activity of the compounds was expressed in terms of the Minimal Inhibitory Concentration (MIC), where the MIC is described as the lowest concentration of the test compound which completely inhibits the growth of the virus.

The compounds of the invention can be prepared for use by incorporating them in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol or oil solutions or oil-water emulsions in the same manner as conventional medicinal substances are prepared.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

Preparation of Amine Intermediates

Preparation I

In three separate runs, 33.8 g. (0.20 mole) portions of 2-benzylpyridine, each in a solution of about 225 ml. of ethanol and 22 ml. of concentrated hydrochloric acid, were reduced over 4.0 g. portions of platinum oxide catalyst under about 54 p.s.i. of hydrogen at a temperature of about 55°–61° C. When reduction was complete in each case, the catalyst was removed by filtration, washed with small portions of ethanol, and the combined filtrates evaporated to a volume of about 80 ml. and diluted to approximately 500 ml. with boiling acetone. The solid which precipitated was collected, washed with acetone and dried giving a combined yield of 124.8 g. of 2-cyclohexylmethylpiperidine hydrochloride, m.p. 211°–213° C. The free base was regenerated from the hydrochloride by neutralization of an aqueous solution of the latter with potassium carbonate, extraction of the oily base into benzene, evaporation of the benzene solution to dryness, and distillation of the residual oil in vacuo at 55°–59° C./0.27 mm. There was thus obtained 89.4 g. of 2-cyclohexylmethylpiperidine.

Preparation 2

A mixture of 15.52 g. (0.10 mole) of 2-phenylpyridine, 15 ml. of concentrated hydrochloric acid and 2.0 g. of platinum oxide in 185 ml. of ethanol in a pressure bottle was heated and shaken in a Parr hydrogenator under 55 p.s.i. of hydrogen at a temperature around 60° C. When reduction was complete in about eight hours, the catalyst was removed by filtration and the filtrate concentrated to about 50 ml. and diluted with 200 ml. of acetone. The solid which separated was collected and dried to give 14.54 g. of 2-cyclohexylpiperidine hydrochloride, m.p. 251°–253° C.

Preparation 3

A mixture of 9.1 g. (0.05 mole) of 2-stilbazole (Shaw et al., J. Chem. Soc. 1933, 77–79) and 1.0 g. of platinum oxide in a solution of 240 ml. of ethanol and 10 ml. of concentrated hydrochloric acid in a pressure bottle was heated and shaken on a Parr hydrogenator under about 55 p.s.i. of hydrogen at a temperature of about 60° C. When reduction was complete in about eight hours, the catalyst was removed by filtration, the filtrate concentrated to a volume of about 50 ml. and diluted with about 200 ml. of acetone. The solid which separated was collected and dried to give 9.6 g. of 2-(2-cyclohexylethyl)-piperidine hydrochloride, m.p. 155°–156° C.

Preparation 4

A solution of 78.1 g. (0.84 mole) of 4-methylpyridine and 89.0 g. (0.84 mole) of benzaldehyde in 103 g. of acetic anhydride was heated with stirring under reflux for twenty-four hours. The mixture was then concentrated to a thick oil in vacuo and the residue dissolved in hot ethanol. The solid which separated was collected and recrystallized from ethanol to give 57.9 g. of 4-styrylpyridine, m.p. 131.5°–133° C.

The latter (36.2 g., 0.2 mole), dissolved in 220 ml. of absolute ethanol and 30 ml. of concentrated hydrochloric acid, was reduced over 3.0 g. of platinum oxide under a hydrogen pressure of about 55 p.s.i. The product was worked up in the manner described above in Preparation 1 and isolated in the form of the hydrochloride salt to give 43.5 g. of 4-(2-cyclohexylethyl)piperidine hydrochloride, m.p. 246°–248° C.

Preparation 5

4-Phenylpyridine (15.5 g., 0.1 mole) dissolved in 185 ml. of absolute ethanol and 15 ml. of concentrated hydrochloric acid was reduced with hydrogen over 2 g. of platinum oxide under a hydrogen pressure of about 55 p.s.i. The product was worked up in the manner described above in Preparation 1 and isolated in the form of the hydrochloride salt to give 15.3 g. of 4-cyclohexylpiperidine hydrochloride. (The free base gives m.p. 106°–109° C.)

Preparation 6

To a mixture of 8.6 g. (0.36 mole) of magnesium turnings in 150 ml. of dry ether was added in small portions with cooling and stirring a solution of 45.0 g. (0.36 mole) of benzyl chloride in 75 ml. of anhydrous ether. When addition was complete, the mixture was stirred for about one hour and then treated dropwise with a solution of 26.6 g. of 4-chlorobutyronitrile in 95 ml. of ether. When addition was complete, the ether was gradually distilled off while replacing with an equal volume of toluene. The mixture was heated under reflux (at about 109° C.) for about 30 minutes, cooled to about 15° C., treated dropwise with 300 ml. of 10% aqueous ammonium chloride, filtered and the organic layer separated. The latter was washed with three 100 ml. portions of dilute hydrochloric acid, and the combined acid extracts were basified with solid potassium carbonate. Extraction of the mixture with ether and removal of the solvent from the combined organic extracts afforded an oil which was distilled in vacuo to give 13.05 g. of 2-benzyl-4,5-dihydropyrrole, b.p. 123°–125° C./13 mm., $n_D^{25}$ 1.5405.

The latter, dissolved in 210 ml. of ethanol and 15 ml. of concentrated hydrochloric acid was reduced with hydrogen over 2 g. of platinum oxide under a hydrogen pressure of about 50 p.s.i. The mixture was worked up in the manner described above in Preparation 1 and the product isolated in the form of the hydrochloride salt to give 16.8 g. of 2-cyclohexylmethylpyrrolidine hydrochloride, m.p. 130.5°–131.5° C. (from acetone).

Preparation 7

To a suspension of 11.2 g. (1.6 mole) of lithium wire in 600 ml. of anhydrous ether was added dropwise 125.6 g. (0.8 mole) of bromobenzene. When addition was complete, the mixture was stirred for about a half hour and then treated dropwise first with a solution of 74.4 g. (0.8 mole) of picoline in 100 ml. of anhydrous ether and then, after stirring for fifteen minutes, with a solution of 74.0 g. (0.4 mole) of 2-phenylethyl bromide in 100 ml. of ether. The mixture was stirred at ambient temperature for about 12 hours and then poured with stirring onto 300 g. of ice. When all excess lithium had reacted, the layers were separated, the aqueous layer washed with additional ether, and the combined organic portions were washed with brine, dried and taken to dryness to give a residual oil which was distilled in vacuo to give 41.3 g. of 2-(3-phenylpropyl)pyridine, b.p. 76°–78° C./0.05 mm., $n_D^{25}$ 1.5592.

The latter (19.7 g., 0.1 mole) dissolved in 235 ml. of ethanol and 15 ml. of concentrated hydrochloric acid was reduced with hydrogen over 2 g. of platinum oxide under a hydrogen pressure of around 55 p.s.i. at about 65° C. The product was worked up in the manner described above in Preparation 1 and isolated in the form of the hydrochloride salt to give 22.2 g. of 2-( 3-cyclohexylpropyl)piperidine hydrochloride, m.p. 175°–176.5° C. (from ethyl acetate).

Preparation 8

Catalytic reduction of 3-benzylpyridine in glacial acetic acid over a platinum oxide catalyst and isolation of the product using the procedure described above in Preparation 1 affords 3-benzylpiperidine.

Preparation of Final Products

EXAMPLE 1

A solution of 25.4 g. (0.1 mole) of α-(3-benzoylphenyl)propionic acid in 40 ml. of benzene was added to 19.8 g. (0.166 mole) of thionyl chloride and the solution refluxed for two and a half hours. The solvent was then removed in vacuo, and the resulting oil (28 g.) consisting of α-(3-benzoylphenyl)-propionyl chloride was dissolved in 40 ml. of diethyl ether and added with stirring over a 30 minute period to a solution of 2-cyclohexylmethylpiperidine in 80 ml. of diethyl ether. The mixture was stirred for about forty-eight hours at ambient temperature, then filtered, the filter washed with ether, and the combined filtrate washed once with dilute acid, once with brine, once with aqueous potassium bicarbonate and evaporated to dryness to give 48.2 g. of 2-cyclohexylmethyl-1-[α-(3-benzoylphenyl)propionyl]-piperidine.

The latter (35.5 g., 0.085 mole) was dissolved in 200 ml. of diethyl ether and the solution added dropwise with stirring to a mixture of 8.08 g. (0.21 mole) of lithium aluminum hydride in 200 ml. of ether while maintaining the temperature at 10°–15° C. The reaction mixture was stirred at ambient temperature for three and one half hours, decomposed by the dropwise addition of 8.1 ml. of water, followed by 8.1 ml. of 15% sodium hydroxide and an additional 22.2 ml. of water. The mixture was then stirred for one hour, filtered, and the filtrate evaporated to dryness to give 34.0 g. of an oil, 10.5 g. of which was chromatographed over 200 g. of alumina and eluted with a solution of 60% hexane/40% ether. The early fractions were removed and evaporated to dryness to give 8.0 g. of 2-cyclohexylmethyl-1-{2-[3-(α-hydroxybenzyl)phenyl]propyl}piperidine as a viscous oil.

Anal. Calcd. for $C_{28}H_{39}NO$: C,82.91; H,9.69; N, 3.45. Found: C,83.12; H,9.80; N,3.49.

EXAMPLES 1A–1D

Following a procedure similar to that described in Example 1, the following compounds of formula I were similarly prepared:

EXAMPLE 1A

2-Cyclohexylmethyl-1-{2-[3-(α-hydroxybenzyl)-phenyl]-ethyl}piperidine, m.p. 122°–124° C. (5.8 g. from benzene/hexane) prepared by reaction of 42 g. (0.16 mole) of 3-benzoylphenylacetyl chloride (German Patent Appln. No. 2,243,444, published Mar. 8, 1944) with 31.7 g. (0.175 mole) of 2-cyclohexylmethylpiperidine in 150 ml. of ether in the presence of 19.4 g. (0.192 mole)

of triethylamine and reduction of the resulting 2-cyclohexylmethyl-1-[(3-benzoylphenyl)acetyl]piperidine (46 g.) with 13 g. (0.35 mole) of lithium aluminum hydride in 325 ml. of ether.

Anal. Calcd. for $C_{27}H_{37}NO$: C,82.81; H,9.52; N,3.58. Found: C,83.01; H,9.54; N,3.52.

EXAMPLE 1B 2,6-Dimethyl-1-{2-[3-(α-hydroxybenzyl)phenyl]ethyl}piperidine, m.p. 115°–117° C. (9.53 g. from benzene/hexane) prepared by reaction of 42 g. (0.16 mole) of 3-benzoylphenylacetyl chloride with 19.8 g. (0.175 mole) of 2,6-dimethylpiperidine in 150 ml. of ether in the presence of 19.4 g. (0.092 mole) of triethylamine and reduction of the resulting 2,6-dimethyl-1-[3-benzoylphenyl)acetyl]piperidine (49 g.) with 13.9 g. (0.365 mole) of lithium aluminum hydride in 300 ml. of ether.

Anal. Calcd. for $C_{22}H_{29}NO$: C,81.69; H, 9.04; N,4.33. Found: C,81.83; H,9.04; N, 4.32.

EXAMPLE 1C

4-[2-(3-Benzoylphenyl)ethyl]morpholine hydrochloride monohydrate, m.p. 177.5°–180° C. (29.0 g. from acetone) prepared by reaction of 46.5 g. (0.18 mole) of 3-benzoylphenylacetyl chloride with 17.2 g. (0.198 mole) of morpholine in 225 ml. of methylene dichloride in the presence of 21.5 g. (0.211 mole) of triethylamine; conversion of the resulting 49 g. of 4-[(3-benzoylphenyl)acetyl]morpholine to the corresponding ethylene glycol ketal by reaction of the former with 125 ml. of ethylene glycol in 1250 ml. of benzene in the presence of 2.5 g. of p-toluenesulfonic acid; and reduction of the resulting ketal (58.6 g.) with 11.8 g. (0.31 mole) of lithium aluminum hydride in 280 ml. of ether, followed by hydrolysis of the ketal by stirring the product at 55°–60° C. with 300 ml. of 1.5N hydrochloric acid for 45 minutes.

Anal. Calcd. for $C_{19}H_{21}NO_2 \cdot HCl \cdot H_2O$: C,65.23; H,6.91; Cl,10.13. Found: C,65.38; H,6.88; Cl,10.19.

EXAMPLE 1D

N-[2-(3-Benzoylphenyl)ethyl]-N-(3-dimethylaminopropyl)amine dihydrochloride hemi-hydrate, m.p. 194°–197° C. (11.1 g. of the free base obtained as a dark oil, a small amount converted to the dihydrochloride) prepared by reaction of 46.3 g. (0.167 mole) of 3-benzoylphenylacetyl chloride with 30.2 g. (0.3 mole) of 3-dimethylaminopropylamine in 200 ml. of methylene dichloride in the presence of 20.1 g. (0.2 mole) of triethylamine; conversion of the resulting 9 g. of N-[(3-benzoylphenyl)acetyl]-N-(3-dimethylaminopropyl)amine to the corresponding ethylene glycol ketal by reaction of 15 g. of the former with 37.5 ml. of ethylene glycol in the presence of 9.75 g. of p-toluenesulfonic acid in 395 ml. of benzene; and reduction of the resulting ketal (15.6 g.) with 3.2 g. (0.084 mole) of lithium aluminum hydride in a solution of 50 ml. of dioxane and 50 ml. of di-n-butyl ether, followed by hydrolysis of the ketal by warming it for one hour in 200 ml. of dilute hydrochloric acid at 55° C.

Anal. Calcd. for $C_{20}H_{26}N_2O \cdot 2HCl \cdot 1/2\ H_2O$: C,61.22; H,7.43; Cl,18.01. Found: C,61.97; H,7.48; Cl,17.70.

EXAMPLE 2

Following a procedure similar to that described in Example 1, 2,6-dimethyl-1-[α-(3-benzoylphenyl)propionyl]piperidine (14.3 g. as an oil) was prepared from 12.7 g. of α-(3-benzoylphenyl)propionic acid, 10 g. (0.084 mole) of thionyl chloride, 6.22 . (0.055 mole) of 2,6-dimethylpiperidine and 6.05 g. (0.06 mole) of triethylamine, and the resulting amide (14.3 g.) reduced with 3.9 g. (0.103 mole) of lithium aluminum hydride in diethyl ether to give 13.2 g. of 2,6-dimethyl- 1-{2-]3-(α-hydroxybenzyl)phenyl]propyl}piperidine as a yellow oil.

Anal. Calcd. for $C_{23}H_{31}NO$: C,82.34; H,8.71; N,4.18. Found: C,82.22, H,8.82; N,4.15.

EXAMPLES 2A-D

Following a procedure similar to that described in Example 1, the following compounds of formula I are similarly prepared:

EXAMPLE 2A

N-t-Butyl-N-{2-[3-(α-hydroxy-4-methyl-2-chlorobenzyl)phenyl]propyl}amine prepared by reaction of α-[3-(4-methyl-2-chlorobenzoyl)phenyl]propionyl chloride with t-butylamine and reduction, with lithium aluminum hydride, of the resulting N-t-butyl-N-{α-[3-(4-methyl-2-chlorobenzoyl)phenyl]propionyl}-amine;

EXAMPLE 2B

N-Benzyl-N-t-butyl-N-{2-[3-(α-hydroxy-3-trifluoromethylbenzyl)phenyl]propyl}amine prepared by reaction of α-[3-(3-trifluoromethylbenzoyl)phenyl]propionyl chloride with N-benzyl-N-t-butylamine and reduction, with lithium aluminum hydride, of the resulting N-benzyl-N-t-butyl-N-{α-[3-(3-trifluoromethylbenzoyl)phenyl]propionyl}amine;

EXAMPLE 2C

N,N-Di-isobutyl-N-{2-[3-(α-hydroxy-2,4-dichlorobenzyl)phenyl]propyl}amine prepared by reaction of α-[3-(2,4-dichlorobenzoyl)phenyl]propionyl chloride with N,N-di-isobutylamine and reduction, with lithium aluminum hydride, of the resulting N,N-di-isobutyl-N-{α-[3-(2,4-dichlorobenzoyl)phenyl]propionyl}amine; and

EXAMPLE 2D 4-(2-Cyclohexylethyl)-1-{2-[3-(α-hydroxy-2-bromobenzyl)-4-methylphenyl]propyl}piperidine prepared by reaction of α-[3-(2-bromobenzoyl)-4-methylphenyl]propionyl chloride with 4-(2-cyclohexylethyl)piperidine and reduction, with lithium aluminum hydride, of the resulting 4-(2-cyclohexylethyl)-1-{α-[3-(2-bromobenzoyl)-4-methylphenyl]propionyl}piperidine.

EXAMPLE 3

To 220 g. (1.65 moles) of aluminum chloride was added with vigorous stirring over a twenty minute period 81 g. (0.67 mole) of acetophenone. The resulting mixture was treated dropwise with stirring over a 40 minute period with 120 g. (0.8 mole) of bromine. When addition was complete, the mixture was stirred for an additional fifteen minutes and then extracted with four 150 ml. portions of ether. The combined ether extracts were washed once with water, once with 10% potassium bicarbonate, once with saturated brine, dried over anhydrous sodium sulfate, and evaporated to dryness to give 141 g. of an oil which was distilled in vacuo to give 108.7 g. of 3-bromoacetophenone, b.p. 71.5°–76° C./0.5 mm.

To 2,200 ml. of isopropanol in a three-necked round bottom flask flushed with nitrogen was added in pieces 60 g. (2.6 moles) of sodium. When all the sodium had dissolved, the mixture was cooled to about 7°-8° C. and treated over a period of thirty minutes with a solution of 318 g. (1.6 moles) of 3-bromoacetophenone and 352 g. (2.88 moles) of ethyl chloroacetate. The mixture was stirred at 7°-8° C. for 5 hours and then at ambient temperature for about 48 hours, refluxed for one hour, distilled to remove about one liter of isopropanol, and the residue diluted with 1900 ml. of water and 1200 ml. of toluene and stirred. The layers were separated, the aqueous layer was extracted with additional toluene, and the combined toluene extracts were washed with saturated brine, dried, and evaporated to dryness to give 558.8 g. of a brown liquid which was combined with a solution of 70 g. of sodium hydroxide in 225 ml. of water and 1200 ml. of absolute ethanol and refluxed for about 12 hours. The mixture was then taken to dryness in vacuo to give 575.6 g. of a solid which was dissolved in water, acidified with dilute hydrochloric acid, and the mixture extracted with benzene. The benzene extracts were taken to dryness to give 485.4 g. of material which was steam distilled affording 272.5 g. of α-(3-bromophenyl)propionaldehyde.

A solution of the latter with 465 g. (2.6 moles) of 2-cyclohexylmethylpiperidine in 6 liters of benzene was refluxed under a Dean-Stark trap for about 12 hours. The solvent was removed in vacuo giving 712.1 . of an oil which was distilled in vacuo to remove lower boiling impurities. There was thus obtained as a higher boiling pot residue 357.2 g. of 2-cyclohexylmethyl-1-[2-(3-bromophenyl)-2-propenyl]piperidine.

The latter (0.95 mole) was dissolved in 3 liters of hexane, and the solution cooled in an ice bath and treated with 220 ml. (1.20 moles) of 4.9N ethereal hydrogen chloride. The white gummy solid which separated, consisting of the iminium hydrochloride, was collected, filtered, washed with fresh hexane, dissolved in 3.5 liters of dimethylformamide, and the solution treated with 72 g. (1.9 moles) of sodium borohydride added in small amounts over a ten minute period. The mixture was then stirred at ambient temperature for about an hour and a half, treated with one liter of 10% sodium hydroxide and 6 liters of water, and then extracted with hexane. The combined hexane extracts afforded 305.4 g. of a yellow oil which was distilled in vacuo to give 189.6 g. of material, b.p. 143°-161° C./0.06 mm., which was redistilled at 0.5 mm. (b.p. 167°-187° C.) to give 158.5 g. of 2-cyclohexylmethyl-1-[2-(3-bromophenyl)propyl]-piperidine.

Anal. Calcd. for $C_{21}H_{32}BrN$: C,66.66; H,8.52; Br,21.12. Found: C,66.71; H,8.36; Br,21.20.

A solution of the latter (37.8 g., 0.1 mole) dissolved in 80 ml. of diethyl ether was treated dropwise with 165 ml. (0.18 mole) of a 1.08M solution of n-butyl lithium in diethyl ether while maintaining the temperature around 10° C. When addition was complete, the mixture was stirred for 30 minutes at about 10° C., then at ambient temperature for 1 hour, refluxed for about 30 minutes, cooled once again to 10° C., and treated with a solution of 25.8 g. (0.19 mole) of 4-methoxybenzaldehyde in 50 ml. of ether while maintaining the temperature around 15°-20° C. The mixture was then refluxed for twenty minutes, cooled, basified by the addition of 110 ml. of 10% sodium hydroxide and stirred for 10 minutes. The mixturewas then filtered, the organic layer separated, and the aqueous layer extracted with additional diethyl ether. The combined organic extracts were washed with saturated brine, dried over sodium sulfate, and evaporated to dryness to give 55 g. of an oil which was dissolved in 150 ml. of absolute methanol. The solution was treated cautiously with 7 g. of sodium borohydride, stirred at 15° C. for 20 minutes, carefully acidified by the addition of 150 ml. of sulfuric acid and extracted three times with hexane. The aqueous solution was basified with 150 ml. of 10% sodium hydroxide, diluted with water and extracted four times with hexane. The combined hexane extracts afforded 32 g. of an oil which was chromatographed on 500 g. of alumina using 1.5% isopropylamine in hexane as eluent. The first 3 liters of eluate were collected and set aside, and the next 3.7 liters collected and evaporated to dryness to give 20.4 g. of 2-cyclohexylmethyl-2-{2-[3-(α-hydroxy-4-methoxybenzyl)phenyl]propyl}piperidine as a yellow oil.

Anal. Calcd. for $C_{29}H_{41}NO_2$: C,79.95; H,9.49; N,3.22. Found: C,78.88; H,9.43; N,3.07.

EXAMPLES 3A-3H

Following a procedure similar to that described in Example 3, the following compounds of formula I are prepared:

EXAMPLE 3A

2-Cyclohexylmethyl-1-{2-[3-(α-hydroxy-3-chlorobenzyl) phenyl]propyl}piperidine (26.8 g. as a yellow oil) prepared by reaction of 37.8 g. (0.1 mole) of 2-cyclohexylmethyl-1-[2-(3-bromophenyl)propyl]piperidine with 0.19 mole of n-butyl lithium and reaction of the resulting lithio derivative with 28.0 g. (0.2 mole) of 3-chlorobenzaldehyde in about 250 ml. of diethyl ether.

Anal. Calcd. for $C_{28}H_{38}ClNO$: C,76.42; H,8.70; N,3.18. Found: C,76.64; H,8.98; N,3.16.

EXAMPLE 3B

2-Cyclohexylmethyl-1-{2-[3-(α-hydroxybenzyl)-phenyl]-propyl}pyrrolidine (5.3 g. as a tan viscous oil) prepared by reaction of 10.8 g. (0.03 mole) of 2-cyclohexylmethyl-1-[2-(3-bromophenyl)propyl]pyrrolidine with 0.06 mole of n-butyl lithium and reaction of the resulting lithio derivative with 7.0 g. (0.066 mole) of benzaldehyde.

Anal. Calcd. for $C_{37}H_{37}NO$: C,82.81; H,9.52; N,3.58. Found: C,82.29; H,10.03; N,3.51.

EXAMPLE 3C

2-Cyclohexylmethyl-1-{2-[3-(α-hydroxy-3,4dichlorobenzyl)phenyl]propyl}piperidine (12.3 g. as an oil) prepared by reaction of 37.8 g. (0.1 mole) of 2-cyclohexylmethyl-1-[2-(3-bromophenyl)propyl]piperidine with 0.19 mole of n-butyl lithium and reaction of the resulting lithio derivative with 35.1 g. (0.2 mole) of 3,4-dichlorobenzaldehyde in diethyl ether.

EXAMPLE 3D

2-Cyclohexylmethyl-1-{2-[3-(α-hydroxy-2-chlorobenzyl)-phenyl]propyl}piperidine (30.7 g. as an oil) prepared by reaction of 37.8 g. (0.1 mole) of 2-cyclohexylmethyl-1-[2-(3-bromophenyl)-propyl]piperidine with 0.19 mole of n-butyl lithium and reaction of the resulting lithio derivative with 28.0 g. (0.2 mole) of 2-chlorobenzaldehyde in diethyl ether.

EXAMPLE 3E 2-(3-Cyclohexylpropyl)-1-{2-[3-(α-hydroxybenzyl)-phenyl]propyl}piperidine (5.4 g. as a viscous oil) prepared by reaction of 12.2 g. (0.03 mole) of 2-(3-cyclohexylpropyl)-1-[2-(3-bromophenyl)propyl]piperidine with 0.68 mole of n-butyl lithium and reaction of the resulting lithio derivative with 7.0 g. (0.06 mole) of benzaldehyde in diethyl ether.

Anal. Calcd. for $C_{30}H_{43}NO$: C,83.09; H,9.99; N,3.23. Found: C,82.92; H,10.26; N,3.19.

EXAMPLE 3F

2-Cyclohexylmethyl-1-{2-[3-(α-hydroxy-4-methylmercaptobenzyl)phenyl]propyl}piperidine prepared by reaction of 2-cyclohexylmethyl-1-[2-(3-bromophenyl)-propyl]piperidine with n-butyl lithium and reaction of the resulting lithio derivative with 4-methylmercaptobenzaldehyde.

EXAMPLE 3G

2-Cyclohexylmethyl-1-{2-[3-(α-hydroxy-4-methylsulfinyl-benzyl)phenyl]propyl}piperidine prepared by reaction of 2-cyclohexylmethyl-1-{2-[3-(α-hydroxy-4-methylmercaptobenzyl)phenyl]-propyl}piperidine described in Example 3F with one molar equivalent amount of hydrogen peroxide in formic acid.

EXAMPLE 3H

2-Cyclohexylmethyl-1-{2-[3-(α-hydroxy-4-methylsulfonylbenzyl)phenyl]propyl}piperidine prepared by reaction of 2-cyclohexylmethyl-1-{2-[33-(α-hydroxy-4-methylmercaptobenzyl)-phenyl[propyl}piperidine described in Example 3F with two molar equivalents of hydrogen peroxide in formic acid.

EXAMPLE 4

Following a procedure similar to that described in Example 3, 18.9 g. (0.05 mole) of 2-cyclohexylmethyl-1-[2-(3-bromophenyl)propyl]piperidine was reacted with 0.1 mole of n-butyl lithium in diethyl ether and the resulting lithio derivative reacted directly with 12.3 g. (0.103 mole) of 4-methylbenzaldehyde to give 16.9 g. of 2-cyclohexylmethyl-1-{2-[3-(α-hydroxy-4-methylbenzyl)phenyl]propyl}piperidine as a yellow oil.

Anal. Calcd. for $C_{29}H_{41}NO$: C,83.00; H,9.85; N,3.34. Found: C,83.04; H,10.01; N,3.31.

EXAMPLE 5

Following a procedure similar to that described in Example 3 above, 18.9 g. (0.05 mole) of 2-cyclohexylmethyl-1-[2-(3-bromophenyl)propyl]piperidine was reacted with 0.1 mole of n-butyl lithium in diethyl ether and the resulting lithio derivative reacted directly with 15.5 g. (0.11 mole) of 4-chlorobenzaldehyde. The crude product was reduced with 4.5 g. (0.12 mole) of sodium borohydride in methanol to give 16.6 g. of 2-cyclohexylmethyl-1-{2-[3-(α-hydroxy-4-chlorobenzyl)phenyl]-propyl}piperidine as an oil.

Anal. Calcd. for $C_{28}H_{38}ClNO$: C.76.42; H,8.70; Cl,8.06. Found: C,76.82; H,8.76; Cl,8.14.

Following a procedure similar to that described in Example 5, the following compound of formula I was similarly prepared:

EXAMPLE 5A

2-Cyclohexylmethyl-1-{2-[3-(α-hydroxy-2,6-dichlorobenzyl)phenyl]propyl}piperidine (yellow oil) prepared by reaction of 18.9 g. (0.05 mole) of 2-cyclohexylmethyl-1-[2-(3-bromophenyl)-propyl]piperidine with 0.1 mole of butyl lithium in diethyl ether followed by 19.2 g. (0.11 mole) of 2,6-dichlorobenzaldehyde to give 19.3 g. of product.

Anal. Calcd. for $C_{28}H_{37}Cl_2NO$: C,70.87; H,7,86; Cl,14.94. Found: C.71.06; H,8.08; Cl,14.81.

EXAMPLE 6

Following a procedure similar to that described in Example 3, 37.8 g. (0.1 mole) of 2-cyclohexylmethyl-1-[2-(3-bromophenyl)propyl]piperidine was reacted with 0.18 mole of n-butyl lithium in diethyl ether and the resulting lithio derivative reacted directly with 27 g. (0.23 mole) of acetophenone to give 11.8 g. of 2-cyclohexylmethyl-1-{2-[3-(α-hydroxy-α-methylbenzyl)phenyl]propyl}piperidine as a yellow oil.

Anal. Calcd. for $C_{29}H_{41}NO$: C,83.00; H,9.85; N,3.34. Found: C,83.34; H,9.97; N,3.23.

EXAMPLE 7

A solution of 0.15 mole of n-butyl lithium in 90 ml. of diethyl ether was prepared by addition of 20.5 g. of n-butyl bromide in 30 ml. of ether to 2.58 g. (0.375 mole) of lithium. Sufficient volume of the solution to provide 0.093 mole was added to a solution of 19.4 g. (0.051 mole) of 2-cyclohexylmethyl-1-[23-(3-bromophenyl)-propyl]piperidine (described above in Example 3) in 100 ml. of ether. The mixture was stirred for 30 minutes while maintaining the temperature below 10° C., refluxed for 30 minutes, cooled once again below 10° C., treated over a 10 minute period with a solution of 13.3 g. (0.10 mole) of 4-methoxybenzonitrile in 80 ml. of ether, stirred for an additional hour and a half at below 10° C., then stirred overnight at ambient temperature and treated with 110 ml. of a solution prepared dissolving 9 ml. of concentrated sulfuric acid in 45 ml. of water and 108 ml. of dioxane. The solution was refluxed for 2 hours, cooled, basified with 100 ml. of 10% sodium hydroxide, the layers separated, and the aqueous layer extracted with ether. The ether extracts were washed with brine, dried and taken to dryness to give 32.6 g. of material which was dissolved in hexane and extracted with a solution of 8 ml. of concentrated sulfuric acid, 136 ml. of water and 144 ml. of methanol. The extracts were rendered basic with 10% sodium hydroxide, the mixture extracted once again with hexane, and the hexane extracts washed with brine, dried and taken to dryness to give 28.1 g. of material which was chromatographed on 400 g. of alumina and eluted with 50% benzene 50% hexane. The first 1750 ml. of eluate was taken to dryness, the residue heated in vacuo at 0.1 mm/222° C. (bath temperature) to drive off some 4-methoxybenzonitrile, and the residue once again chromatographed on alumina (250 g.) using 15% ether/85% hexane. The first 400 ml. of eluate was discarded and the next 1200 ml., on evaporation to dryness, afforded 7.1 g. of 2-cyclohexylmethyl-1-{2-[3-(4-methoxy-benzoyl)phenyl]propyl}piperidine as a yellow oil.

Anal. Calcd. for $C_{29}H_{39}NO_2$: C,80.33; H,9.07; N,3.23. Found: C,80.50; H,9.17; N,3.14.

EXAMPLES 7A-7L

Follown g a procedure similar to that described in Examples 3, 4 and 5, the following compounds of formula I are similarly prepared:

EXAMPLE 7A

2-Cyclohexylmethyl-1-[2-(3-benzoylphenyl)propyl]-pyrrolidine, (viscous amber liquid) prepared by reaction of 21.3 g. (0.1 mole) of α-(3-bromophenyl)propionaldehyde with 31.4 g. (0.2 mole) of 2-cyclohexylmethyl piperidine in benzene; conversion of the resulting 33.7 g. of 1-[2-(3-bromophenyl)-1-propenyl]pyrrolidone to the iminium chloride with ethereal hydrogen chloride;

reduction of the iminium chloride (34.0 g.) with 6.4 g. (0.17 mole) of sodium borohydride in dimethylformamide; reaction of 9.8 g. (0.027 mole) of the resulting (18.8 g.) 2-cyclohexylmethyl-1-[2-(3-bromophenyl)propyl]-pyrrolidine (b.p. 135°–136° C./0.02 mm.) with 0.05 mole of butyl lithium followed by 6.2 g. (0.06 mole) of benzonitrile in diethyl ether and decomposition of the product with a solution of 4 ml. of concentrated sulfuric acid in 20 ml. of water and 50 ml. of dioxane to give 5.1 g. of product.

Anal. Calcd. for $C_{27}H_{35}NO$: C,83.24; H,9.06; N,3.60. Found: C,82.77; H,9.05; N,3.64.

EXAMPLE 7B

2-Cyclohexylmethyl-1-{2-{2-[3-(4-fluorobenzoyl)-phenyl]-propyl}piperidine (yellow oil) prepared by reaction of 18.9 g. (0.05 mole) of 2-cyclohexylmethyl-1-[2-(3-bromophenyl)propyl]-piperidine with 0.1 mole of butyl lithium in diethyl ether followed by 12.8 g. (0.11 mole) of 4-fluorobenzonitrile and decomposition of the product with a solution of 3.8 ml. of concentrated sulfuric acid in 19 ml. of water and 45 ml. of dioxane to give 6.5 g. of product.

Anal. Calcd. for $C_{28}H_{36}FNO$: C,79.77; H,8.61; N,3.32. Found: C,79.60; H,8.76; N,3.51.

EXAMPLE 7C

2-Cyclohexylmethyl-1-{2-{2-[3-(4-methylbenzoyl)-phenyl]-propyl}piperidine (9.7 g. as a yellow oil) prepared by reaction of 18.9 g. (0.05 mole) of 2-cyclohexyl-methyl-1-[2-(3-bromophenyl)-propyl]piperidine with 0.1 mole of butyl lithium in diethyl ether followed by 12.4 g. (0.11 mole) of 4-methyolbenzonitrile and decomposition of the product with a solution of 3.8 ml. of concentrated sulfuric acid in 19 ml. of water and 45 ml. of dioxane to give 9.7 g. of product.

Anal. Calcd. for $C_{29}H_{39}NO$: C,83.40; H,9.41; N,3.35. Found: C,83.34; H,9.61; N,3.30.

EXAMPLE 7D 2-(3-Cyclohexylpropyl)-1-[2-(3-benzoylphenyl)-propyl]-piperidine (yellow oil) prepared by reaction of 12.2 g. (0.03 mole) of 2-(3-cyclohexylpropyl)-2-[2-(3-bromophenyl)propyl]-piperidine with 0.06 nole of butyl lithium in diethyl ether followed by 72.2 g. (0.07 mole) of benzonitrile and decomposition of the product with a solution of 8.3 ml. of concentrated sulfuric acid in 42 ml. of water and 100 ml. of dioxane to give 6.2 g. of product.

Anal. Calcd. for $C_{30}H_{41}NO$: C,83.47; H,9.57; N,3.24. Found: C,83.28; H,9.77; N,3.05.

EXAMPLE 7E

2-Cyclohexyl-1-[2-(3-benzoylphenyl)propyl]piperidine (light tan oil) prepared by reaction of 12.7 g. (0.035 mole) of 2-cyclohexyl-1-[2-(3-bromophenyl)propyl]-piperidine with 0.07 mole of butyl lithium in diethyl ether followed by 8.9 g. (0.077 mole) of benzonitrile and decomposition of the product with a solution of 9 ml. of concentrated sulfuric acid in 45 ml. of water and 10 ml. of dioxane to give 6.1 g. of product.

Anal. Calcd. for $C_{27}H_{35}NO$: C,83.24; H,9.06; N,3.60. Found: C,83.16; H,9.16; N,3.44.

EXAMPLE 7F 2-(2-Cyclohexylethyl)-1-[2-(3-benzoylphenyl)-propyl]-piperidine (pale tan liquid) prepared by reaction of 13.7 g. (0.035 mole) of 2-(2-cyclohexylethyl)-1-[2-(3-bromophenyl)propyl]-piperidine with 0.07 mole of butyl lithium in diethyl ether followed by 8.9 g. (0.077 mole) of benzonitrile and decomposition of the product with a solution of 9 ml. of concentrated sulfuric acid in 45 ml. of water and 100 ml. of dioxane to give 8.9 g. of product.

Anal. Calcd. for $C_{29}H_{39}NO$: C, 83.40; H, 9.41; N, 3.35. Found: C, 83.57; H,9.40; N, 3.35.

EXAMPLE 7G

8-[2-(3-Benzoylphenyl)propyl]-1,4-dioxa-8-azaspiro[4,5]decane (pale yellow oil) prepared by reaction of 10.6 g. (0.05 mole) of α-(3-bromophenyl)propionaldehyde with 14.3 g. (0.1 mole) of 1,4-dioxa-8-azaspiro[4,5]decane in benzene; conversion of the resulting 15.7 g. of 8-[2-(3-bromophenyl)-1-propenyl]-1,4-dioxa-8-azaspiro[4,5]decane to the iminium chloride with ethereal hydrogen chloride; reduction of the iminium chloride with 3.8 g. (0.08 mole) of sodium borohydride in dimethylformamide; reaction of the resulting 17.5 g. (0.05 mole) of 8-[2-(3-bromophenyl)-propyl]-1,4-dioxa-8-azaspiro[4,5]decane with 0.1 mole of butyl lithium followed by 15.5 g. (0.15 mole) of benzonitrile in diethyl ether and decomposition of the product with a solution of 6 ml. of concentrated sulfuric acid in 30 ml. of water and 72 ml. of dioxane to give 5.1 g. of product.

Anal. Calcd. for $C_{23}H_{27}NO_3$: C,75.58; H, 7.45; N, 3.83 Found: C,75.60; H,7.69; N,3.87.

EXAMPLE 7H

4-[2-(3-Benzoylphenyl)propyl]morpholine (pale yellow oil) prepared by reaction of 21.3 g. (0.1 mole) of α-(3-bromophenyl)propionaldehyde with 17.4g. (0.2 mole) of morpholine in benzene; conversion of the resulting 27.3 g. of 4-[2-(3-bromophenyl)-1-propenyl]morpholine to the iminium chloride with ethereal hydrogen chloride; reduction of the iminium chloride with 7.6 g. (0.2 mole) of sodium borohydride in dimethylformamide; reaction of the resulting 19 g. of 4-[2-(3-bromophenyl)propyl]-morpholine (b.p. 99°–120° C./0.09 mm., $n_D^{24}=1.5477$) with 0.1 mole of butyl lithium followed by 15.5 g. (0.15 mole) of benzonitrile in diethyl ether and decomposition of the product with 150 ml. of a solution made by dissolving 6 ml. of concentrated sulfuric acid in 30 ml. of water and 72 ml. of dioxane to give 7.5 g. of product.

Anal. Calcd. for $C_{20}H_{23}NO_2$: C,77.64; H,7.49; N,4.53. Found: C,77.62, H,7.37; N,4.71.

A small amount of the free base was converted to the hydrochloride salt to give 4-[2-(3-benzoylphenyl)-propyl]morpholine hydrochloride monohydrate, m.p. 151°–155° C.

Anal. Calcd. for $C_{20}H_{23}NO_2.HCl.H_2O$: C,66.02; H,7.20; Cl,9.74. Found: C,66.37; H,7.24; Cl,9.59.

EXAMPLE 7J 2,6-Dimethyl-4-[2-(3-benzoylphenyl)propyl]morpholine cyclohexanesulfamate prepared by reaction of 21.3 g. (0.1 mole) of α-(3-bromophenyl)propionaldehyde with 23 g. (0.2 mole) of 2,6-dimethylmorpholine in benzene; conversion of the resulting 28.4 g. of 2,6-dimethyl-4-[2-(3-bromophenyl)-1-propenyl]morpholine to the iminium chloride with ethereal hydrogen chloride; reduction of the iminium chloride with 10 g. (0.26 mole) of sodium borohydride in dimethylformamide; reaction of the resulting 15.5 g. of 2,6-dimethyl-4-[2-(3-bromophenyl)propyl]morpholine (b.p. 125°–129° C./0.01 mm., $n_D^{24}=1.5294$) with 0.1 mole of butyl lithium followed by 11 g. (0.11 mole) of benzonitrile in diethyl ether and decomposition of the product with 150 ml. of a solution prepared by dissolving 45 ml. of concentrated sulfuric acid in 225 ml. of water and 540 ml. of dioxane. The product was converted to the cyclohexanesulfamate salt which was recrystallized from acetone to give 7.7 g. of product, m.p. 156–158° C.

Anal. Calcd. for $C_{22}H_{27}NO_2 \cdot C_6H_{13}NO_3S$: C,65.08; H,7.80; S,6.20. Found: C,64.86; H,7.72; S,6.22.

EXAMPLE 7K

2-Cyclohexylmethyl-1-[2-[3-benzoyl-2-methylphenyl)-ethyl]piperidine prepared by reaction of 2-bromo-6-bromomethyl-toluene [described by Lindsay et al., J. Am. Chem. Soc. 83, 943–949 (1961)] with potassium cyanide in refluxing ethanol; reduction of the resulting (3-bromo-2-methylphenyl)acetonitrile with diisobutylaluminum hydride; reaction of the resulting (3-bromo-2-methylphenyl)acetaldehyde with 2-cyclohexylmethylpiperidine in refluxing benzene under a Dean-Stark trap; reduction with sodium borohydride of the iminium hydrochloride of the resulting 2-cyclohexylmethyl-1-[2-(3-bromo-2-methylphenyl)-1-ethenyl]piperidine; and reaction of the resulting 2-cyclohexylmethyl-1-[2-(3-bromo-2-methylphenyl)ethyl]piperidine with n-butyl lithium in diethyl ether followed by reaction of the resulting lithio derivative with benzonitrile.

EXAMPLE 7L

4-[2-(3-Benzoyl-2-methylphenyl)ethyl]morpholine prepared by reaction of (3-bromo-2-methylphenyl)acetaldehyde with morpholine in refluxing benzene under a Dean-Stark trap; reduction with sodium borohydride of the iminium hydrochloride of the resulting 4-[2-(3-bromo-2-methylphenyl)-1-ethenyl]-morpholine; and reaction of the resulting 4-[2-(3-bromo-2-methylphenyl)ethyl]morpholine with n-butyl lithium in diethyl ether followed by reaction of the resulting lithio derivative with benzonitrile.

EXAMPLE 8

Following a procedure similar to that described in Example 7. 18.9 g. (0.05 mole) of 2-cyclohexylmethyl-1-[2-(3-bromophenyl)propyl]piperidine was reacted with 0.095 mole of n-butyl lithium in diethyl ether and the resulting lithio derivative reacted directly with 12.4 g. (0.106 mole) of 2-methylbenzonitrile to give 4.85 g. of 2-cyclohexylmethyl-1-{2-[3-(2-methylbenzoyl)phenyl]-propyl}piperidine as a yellow oil.

Anal. Calcd. for $C_{29}H_{39}NO$: C,83.40; H,9.41; N,3.35. Found: C,83.14; H,9.54; N,3.67.

EXAMPLE 9

Following a procedure similar to that described in Example 7, 18.9 g. (0.05 mole) of 2-cyclohexylmethyl-1-[2-(3-bromophenyl)propyl]piperidine was reacted with 0.095 mole of n-butyl lithium in diethyl ether and the resulting lithio derivative reacted directly with 12.4 g. (0.106 mole) of 3-methylbenzonitrile to give 10.7 g. of 2-cyclohexylmethyl-1-{2-[3-(3-methylbenzoyl)phenyl]-propyl}piperidine as a yellow oil.

Anal. Calcd. for $C_{29}H_{39}NO$: C,83.40; H,9.41; N,3.35. Found: C,83.06; H,9.38; N,3.48.

EXAMPLE 10

A solution of 13.0 g. (0.032 mole) of 2-cyclohexylmethyl-1-{2-[3-(}-hydroxybenzyl)phenyl]propyl}· piperidine (described above in Example 1) in 167 ml. of glacial acetic acid and 33 ml. of perchloric acid was placed in a parr hydrogenator and reduced over 3.5 g. of 10% palladium-on-charcoal at ambient temperature under a hydrogen pressure of 54 p.s.i. When reduction was complete, the catalyst was removed by filtration, the filtrate was taken to dryness, and the residue rendered basic with 10% sodium hydroxide and extracted four times with hexane. The combined hexane extracts were dried, taken to dryness, and the residue chromatographed on 220 g. of alumina, and eluted with 10% ether/89% hexane/1% isopropylamine. The first 350 ml. of eluate when taken to dryness afforded 10.6 g. of 2-cyclohexylmethyl-1-[2-(3-benzylphenyl)propyl]-piperidine as a yellow oil.

Anal. Calcd. for $C_{28}H_{39}N$: C, 86.32; H,10.09; N,3.59. Found: C,86.18; H,10.34; N,3.51.

EXAMPLE 11

Following a procedure similar to that described in Example 10, 11.1 g. (0.027 mole) of 2-cyclohexylmethyl-1-{2-[3-(α-hydroxy-α-methylbenzyl)phenyl]phenyl propyl}piperidine (described in Example 6) dissolved in 180 ml. of glacial acetic acid and 20 ml. of 72% perchloric acid was reduced with hydrogen over 0.8 g. of palladium-on-charcoal to give 10.3 g. of 2-cyclohexylmethyl-1{2-[3-(α-methylbenzyl)phenyl]propyl}piperidine as a yellow oil.

Anal. Calcd. for $C_{29}H_{41}N$: C,86.29; H,10.24; N,3.47. Found: C,86.04; H,10.21; N,3.70.

EXAMPLE 12

A solution of 26.8 g. (0.066 mole) of 2-cyclohexylmethyl-1-2-[3-(α-hydroxybenzyl)phenyl]propyl}piperidine (described above in Example 1) in 140 ml. of benzene was vigorously stirred and cooled to 16° C. and then treated dropwise ovr a period of ten minutes with 58 ml. of a solution prepared by dissolving 26.7 g. of chromium trioxide in 23 ml. of concentrated sulfuric acid and diluting with water to 100 ml. The mixture was stirred with cooling for about one hour and 45 minutes, the benzene layer removed, and the aqueous layer made basic by addition of 120 ml. of 10% sodium hydroxide and extracted with benzene. The organic extracts, on washing once with dilute alkali, once with brine, and evaporation to dryness, afforded 21.8 g. of an oil which was chromatographed over 300 g. of alumina using 3% isopropylamine in hexane as eluent. The first 600 ml. of eluate was collected and taken to dryness to give 16.2 g. of 2-cyclohexylmethyl-1-[2-(3-benzoylphenyl)propyl]-piperidine as a pale yellow viscous oil.

Anal. Calcd. for $C_{28}H_{37}NO$: C,83.33; H,9.23; N,3.47. Found: C,83.30; H,9.33; N,3.45.

EXAMPLE 13

Following a procedure similar to that described in Example 12, 15.2 g. (0.39 mole) of 2,6-dimethyl-1-{2-[3-(α-hydroxybenzyl)phenyl]propyl}piperidine (described above in Example 2) was oxidized with 34 ml. of a solution prepared by dissolving 13.4 g. of chromium trioxide in 11.5 ml. of concentrated sulfuric acid and dilution with water to 50 ml. The product, in the form of the free base, was purified by chromatographing on alumina using 10% ether/3% isopropylamine/87% hexane as eluent. There was thus obtained 4.8 g. of 2,6-dimethyl-1-[2-(3-benzoylphenyl)propyl]piperidine as a colorless viscous oil.

Anal. Calcd. for $C_{23}H_{29}NO$: C,82.34; H,8.71; N,4.18. Found: C,82.23; H,8.82; N,4.15.

EXAMPLES 13A–13G

Proceeding in a manner similar to that described in Examples 1 and 12, the following compounds of formula I are obtained:

EXAMPLE 13A

2-Methyl-1-[2-(3-benzoylphenyl)propyl]hexamethyleneimine prepared by reaction of α-(3-benzoylphenyl)propionyl chloride with 2-methylhexamethyleneimine [Mueller et al., Monatsh. 61. 212–218 (1932)]; reduction with lithium aluminum hydride of the resulting 2-methyl-1-[α-(3-benzoylphenyl)-propionyl]-hexamethyleneimine; and chromic acid oxidation of the resulting 2-methyl-1-{2-[3-(α-hydroxybenzyl)phenyl]-propyl}-hexamethyleneimine.

EXAMPLE 13B

4-Cyclohexl-1-[2-(3-benzoylphenyl)propyl]-piperidine prepared by reaction of α-(3-benzoylphenyl)propionyl chloride with 4-cyclohexylpiperidine; reduction with lithium aluminum hydride of the resulting 4-cyclohexyl-1-[α-(3-benzoylphenyl)propionyl]piperidine; and chromic acid oxidation of the resulting 4-cyclohexyl-1-{2-[3-(α-hydroxybenzyl)phenyl]propyl}-piperidine.

EXAMPLE 13C

3-Butyl-4-[2-(3-benzoylphenyl)propyl]morpholine prepared by reaction of α-(3-benzoylphenyl)propionyl chloride with 3-butylmorpholine; reduction with lithium aluminum hydride of the resulting 3-butyl-4-[α-(3-benzoylphenyl)propionyl]morpholine; and chromic acid oxidation of the resulting 3-butyl-4-{2-[3-(α-hydroxybenzyl)phenyl]propyl}morpholine.

EXAMPLE 13D

3-Ethyl-4-[2-(3-benzoylphenyl)propyl]thiomorpholine prepared by reaction of α-(3-benzoylphenyl)propionyl chloride with 3-ethylthiomorpholine; conversion of the resulting 3-ethyl-4-[α-(3-benzoylphenyl)propionyl]thiomorpholine to the corresponding ethylene glycol ketal; reduction with lithium aluminum hydride of the resulting ketal; and hyrolysis with dilute mineral acid of the resulting 3-ethyl-4-[2-(3-benzoylphenyl)-propyl]thiomorpholine ethylene glycol ketal.

EXAMPLE 13E

4-Methyl-1-[2-(3-benzoylphenyl)propyl]piperazine prepared by reaction of α-(3-benzoylphenyl)propionyl chloride with 1-methylpiperazine; reduction with lithium aluminum hydride of the resulting 4-methyl-1-[α-(3-benzoylphenyl)propionyl]piperazine; and chromic acid oxidation of the resulting 4-methyl-1-{2-[3-(α-hydroxybenzyl)phenyl]propyl}piperazine.

EXAMPLE 13F

3-Benzyl-1-[2-(3-benzoylphenyl)propyl]piperidine prepared by reaction of α-(3-benzoylphenyl)propionyl chloride with 3-benzylpiperidine; reduction with lithium aluminum hydride of the resulting 3-benzyl-1-[α-(3-benzoylphenyl)propinyl]piperidine; and chromic acid oxidation of the resulting 3-benzyl-1-{2-[3-(α-hydroxybenzyl)phenyl]propyl}piperidine.

EXAMPLE 13G

N-[5-(N′,N′-DImethylamino)-2-pentyl]-N-[2-(3-benzoylphenyl)propyl]amine prepared by reaction of α-(3-benzoylphenyl)propionyl chloride with 5-(N′,N′-dimethylamino)-2-pentylamine; reduction with lithium aluminum hydride of the resulting N-[5-(N′,N′-dimethylamino)-2-pentyl]N-[α-(3-benzoylphenyl)-propionyl]amine; and chromic acid oxidation of the resulting N-[5-(N′,N′-dimethylamino)-2-pentyl]-N-{2-[3-(α-hydroxybenzyl)-phenyl]propyl}amine.

EXAMPLE 14

Following a procedure similar to that described in Example 7, 5.0 g. (13.2 mole) of 2-cyclohexylmethyl-1-[2-(3-bromophenyl)propyl]piperidine was reacted with 0.026 mole of n-butyl lithium in diethyl ethr and the resulting lithio derivative reacted directly with benzonitrile to give 4.0 g. of 2-cyclohexylmethyl-1-[2-(3-benzoylphenyl)propyl]piperidine identical with the material described in Example 12.

EXAMPLE 15

A mixture of 37.5 g. (0.093 mole) of 2-cyclohexylmethyl-1-[2-(3-benzoylphenyl)propyl]piperidine (described in Examples 12 and 14 above) and 10.0 g. (0.14 mole) of hydroxylamine in 125 ml. of 95% ethanol and 25 ml. of water was treated with stirring with 19.4 g. of powdered sodium hydroxide and the mixture refluxed for a half hour. The mixture was then cooled, diluted with hexane, the aqueous layer separated, and the organic layer, after drying, was evaporated to dryness to give 41.6 g. of a yellow oil which was chromatographed on alumina in 30:70 diethyl ether/hexane to give 37.3 g. of 2-cyclohexyl- methyl-1-[2-(3-benzoylphenyl)propyl]-piperidine oxime as an oil.

Anal. Calcd. for $C_{28}H_{38}N_2O$: C,80.33; H,9.15; N,6.69. Found: C,80.03; H,9.42; N,6.44.

EXAMPLES 15A-15C

Following a procedure similar to that described in Example 15, the following compounds of formula I were similarly prepared:

EXAMPLE 15A

4-[2-(3-Benzoylphenyl)ethyl]morpholine oxime (m.p. 117°–134° C., from benzene/hexane) prepared by reacting 18.15 g. (0.05 mole) of 4-[2-(3-benzoylphenyl)ethyl]morpholine hydrochloride with 5.6 g. (0.08 mole) of hydroxylamine hydrochloride in the presence of 12.5 g. (0.31 mole) of sodium hydroxide in 70 ml. of ethanol and 18.5 ml. of water to give 14.06 g. of product.

Anal. Calcd. for $C_{19}H_{22}N_2O_2$: C,73.52; H,7.14; N,9.03. Found: C,73.79; H,7.26; N,8.72.

EXAMPLE 15B 4-(3-Benzoylphenyl)methylmorpholine oxime (m.p. 145–167° C.) prepared by reaction of 28.62 g. (0.09 mole) of 4-(3-benzoylphenyl)methylmorpholine hydrochloride with 9.63 g. (0.14 mole) of hydroxylamine hyrochloride in the presence of 21.68 g. (0.54 mole) of sodium hydroxide in 35 ml. of ethanol and 27 ml. of water to give 13.9 g. of product.

EXAMPLE 15C

4-[2-(3-Benzoylphenyl)propyl]morpholine oxime (m.p. 117°–130° C., for isopropanol) prepared by reaction of 27 g. (0.078 mole) of 4-[2-(3-benzoylphenyl)propyl]morpholine hydrochloride with 8.2 g. (0.117 mole) of hydroxylamine hydrochloride in the presence of 18.8 g. (0.47 mole) of sodium hydroxide in 115 ml. of ethanol and 27 ml. of water to give 3.2 g. of product.

EXAMPLE 16

A solution of 17 g (0.041 mole) of the 2-cyclohexylmethyl-1-[2-(3-benzoylphenyl)propyl]piperidine oxime described above in Example 15 in 110 ml. of ethanol was brought to reflux and treated with 10 g. (0.043 mole) of sodium metal, added in small pieces. Refluxing was continued until all sodium had dissolved, and the solution was then cooled, diluted with 140 ml. of water, evaporated to a volume of about 150 ml. in vacuo, and then extracted with three portions of benzene. Evaporation of the benzene extracts to dryness afforded 14.2 g. of an oil which was converted to the acetate salt by dissolving in chloroform, adding glacial acetic acid and evaporation to dryness. The acetate salt was again dissolved in chloroform and chromatographed on alumina, eluting with chloroform. The acetate hydrolyzed on the column, and the free base obtained from the eluate was dissolved in ethanol, and the solution acidified with ethereal hydrogen chloride and evaporated to dryness to give 6.38 g. of 2-cyclohexylmethyl-1-{2-[3-(α-aminobenzyl)phenyl]propyl}piperidine dihydrochloride, m.p. 167°–195° C.

Anal. Calcd. for $C_{28}H_{41}N_2.2HCl$: N,5.87; Cl,14.85. Found: N,5.61; Cl,14.66.

EXAMPLE 16A–16C

Following a procedure similar to that described in Example 16, the following compounds of formulas I and Ia were similarly prepared:

EXAMPLE 16A

4-{2-[3-(α-Aminobenzyl)phenyl]ethyl}morpholine dihydrochloride, m.p. 260°–263° C. (15.42 g. from methanol/diethyl ether) prepared by reducing 14.55 g. (0.047 mole) of 4-[2-(3-benzoylphenyl)ethyl]morpholine oxime with 11.5 g. (0.50 mole) of sodium in 100 ml. of absolute ethanol.

Anal. Calcd. for $C_{19}H_{24}N_2O.2HCl$: C,61.79; H,7.10; Cl,19.20. Found: C,61.88; H,6.90; Cl,19.16.

EXAMPLE 16B

4-{[3-[3-(α-Aminobenzyl)phenyl]methyl}morpholine dihydrochloride monohydrate, m.p. 270°–274° C. (8.3 g., from methanol/ether) prepared by reduction of 8.12 g. (0.027 mole) of 4-[(3-benzoylphenyl)methyl]morpholine oxime with 6.45 g. (0.28 mole) of sodium in absolute ethanol.

Anal. Calcd. for $C_{18}H_{22}N_2O.2HCl.H_2O$: C,60.84; H,6.81; Cl,19.96. Found: C,60.68; H,6.83; Cl,20.27.

EXAMPLE 16C

4-{2-[3-(α-Aminobenzyl)phenyl]propyl}morpholine dihydrochloride m.p. 255°–265° C. (9.5 g., from methanol/diethyl ether) prepared by reduction of 10.0 g. (0.03 mole) of 4-[2-(3benzoylphenyl)propyl]morpholine oxime with 7.1 g. (0.31 mole) of sodium in 65 ml. of absolute ethanol.

Anal. Calcd. for $C_{20}H_{26}N_2O.2HCl$: C,62.66; H,7.36; Cl,18.50. Found: C,61.78; H,7.17; Cl,18.01.

EXAMPLE 17

A solution of 13.0 g. (0.031 mole) of 2-cyclohexylmethyl-1-{2-[3-(α-hydroxy-α-methylbenzyl)phenyl]propyl}piperidine (described in Example 6) in 130 ml. of methanol and 3 ml. of concentrated sulfuric acid was stirred and refluxed for forty-five minutes, then cooled, diluted with 100 ml. of water, basified with 5 ml. of 35% sodium hydroxide and extracted with hexane. The combined hexane extracts, on washing with brine, drying and evaporation to dryness gave 14.2 g. of an oil which was chromatographed on 260 g. of alumina in 8:92 diethyl ether/hexane. There was thus obtained 9.8 g. of 2-cyclohexylmethyl-1-{2-[3-(1-phenyl-1-vinyl)phenyl]propyl}piiperidine as an oil.

Anal. Calcd. for $C_{29}H_{39}N$: C,86.72; H,9.79; N,3.49. Found: C,86.79; H,9.76; N,3.28.

EXAMPLE 18

4-Methoxyphenylacetic acid (41.5 g., 0.25 mole) was converted to the corresponding acid chloride with 47.7 g. (0.4 mole) of thionyl chloride in benzene using the procedure described above in Example 1. The acid chloride thus produced (36.8 g., 0.2 mole) was reacted with 24.1 g. (0.21 mole) of 2,6-dimethylpiperidine in ether in the presence of 24.2 g. (0.24 mole) of triethylamine using the procedure described above in Example 1. The resulting 2,6-dimethyl-1-[(4-methoxyphenyl)acetyl]piperidine (38.8 g., 0.15 mole) was reduced with lithium aluminum hydride and the product isolated in the form of the hydrochloride salt to give 15.32 g. of 2,6-dimethyl-1-[2-(4-methoxyphenyl)ethyl]piperidine hydrochloride, m.p. 195°–200° C.

The latter (1.0 g., 0.004 mole), in the form of the free base, was added in small portions to a stirred mixture of 1.21 g. (0.009 mole) of aluminum chloride and 1.28 g. (0.009 mole) of benzoyl chloride. The resulting viscous mixture was stirred for about twelve hours at ambient temperature and then mixed with ice, 2 ml. of concentrated hydrochloric acid and 2 ml. of water. The resulting mixture was extracted with chloroform, and the chloroform extracts washed with brine, dried and evaporated to dryness to give 2,6-dimethyl-1-[2-(3-benzoyl-4-methoxyphenyl)ethyl]piperidine as a yellow oil.

EXAMPLe 19

A mixture of 45 g. (0.13 mole) of 2,6-dimethyl-1-[2-(3-benzoyl-4-methoxyphenyl)ethyl]piperidine (described above in Example 18) and 34.9 g. (0.26 mole) of aluminum chloride in tetrachloroethane was heated and stirred at 50° C. for about twelve hours and then poured into a solution of 30 ml. of concentrated hydrochloric acid and 30 ml. of ice water. The mixture was basified with sodium carbonate, extracted four times with chloroform, and the chloroform extracts washed with saturated brine, dried and evaporated to dryness to give crude product which was once again heated for twelve hours at 50° C. with 30 g. of aluminum chloride and 30 ml. of tetrachloroethane. On working up as before, there was obtained 8 g. of crude material which was dissolved in chloroform. The organic solution was washed five times with 10% sodium carbonate, once with brine, then dried and taken to dryness. The residue was dissolved in acetone, and the solution was treated with ethereal hydrogen chloride to give solid material which was recrystallized from isopropanol. There was thus obtained 5.8 g. of 2,6-dimethyl1-[2-(3-benzoyl-4-hydroxyphenyl)ethyl]piperidine hydrochloride, m.p. 217°-219° C.

Anal. Calcd. for $C_{22}H_{27}NO_2.HCl$: C,70.67; H,7.55; N,3.75. Found: C,70.87; H,7.58; N,3.73.

EXAMPLE 20

A solution of 13.2 g. (0.03 mole) of 2-cyclohexylmethyl-1-{2-[3-(α-hydroxy-4-chlorobenzyl)phenyl]propyl}piperidine (described above in Example 5), 16 ml. of concentrated nitric acid and 32 ml. of 501 % perchloric acid in 160 ml. of 1,2-dimethoxyethane was heated under reflux for one and a quarter hours, then cooled, diluted with 50 ml. of water, basified with 150 ml. of 10% sodium hydroxide and extracted with hexane. The hexane extracts were washed once with water, once with brine, dried and evaporated to dryness to give 12 g. of crude product which was chromatographed on 200 g. of alumina using 10:90 ether/hexane as eluent. The first 75 ml. of eluate was discarded and the next 600 ml. was taken to dryness to yield 9.2 g. of 2-cyclohexylmethyl-1-{2-[3-(4-chlorobenzoyl)phenyl]propyl}piperidine.

Anal. Calcd. for $C_{28}H_{36}ClNO$: C,76.77; H,8.28; Cl,8.09. Found: C,76.85; H,8.35; Cl,8.27.

EXAMPLES 20A-20D

Following a procedure similar to that described in Example 20, the following compounds of formula I were similarly prepared:

EXAMPLE 20A

2-Cyclohexylmethyl-1-[2-(3-benzoylphenyl)ethyl]piperidine (yellow oil) prepared by oxidation of 14.0 g. (0.03 mole) of 2-cyclohexylmethyl-1-{2-[3-(α-hydroxybenzyl)phenyl]ethyl}piperidine (described above in Example 1A) in 227 ml. of a solution prepared by dissolving 44.5 ml. of 72% perchloric acid, 20 ml. of water and 32 ml. of concentrated nitric acid in 320 ml. of 1,2-dimethoxyethane. There was thus obtained 8.74 g. of product.

Anal. Calcd. for $C_{27}H_{35}NO$: C,83.24; H,9.06; N,3.60. Found: C,83.46; H,9.26; N,3.75.

EXAMPLE 20B

2-Cyclohexylmethyl-1-{2-[3-(3-chlorobenzoyl)phenyl]propyl}piperidine (yellow oil) prepared by oxidation of 17.0 g. (0.039 mole) of 2-cyclohexylmethyl-1-}-3-(α-hydroxy-3-chlorobenzyl)phenyl]propyl}piperidine (described above in Example 3A) in 244 ml. of a solution prepared by dissolving 48 ml. of 50% perchloric acid and 24 ml. of concentrated nitric acid in 240 ml. of 1,2-dimethoxyethane. There was thus obtained 9.65 g. of product.

Anal. Calcd. for $C_{28}H_{36}ClNO$: C,76.77; H,8.28; N,3.20. Found: C,76.86; H, 8.36; N, 3.13.

EXAMPLE 20C

2-Cyclohexylmethyl-1-{2-[3-(3,4-dichlorobenzoyl)phenyl]propyl}piperidine (yellow oil) prepared by oxidation of 11.9 g. (0.25 mole) of 2-cyclohexylmethyl-1-{2-(3-(α-hydroxy-3,4-dichlorobenzyl)phenyl}piperidine (described above in Example 3C) in 156 ml. of a solution prepared by dissolving 24 ml. of 50% perchloric acid and 12 ml. of concentrated nitric acid in 120 ml. of 1,2-dimethoxyethane. There was thus obtained 5.2 g. of product.

Anal. Calcd. for $C_{28}H_{35}Cl_2NO$: C,71.18; H,7.47; N,2.96. Found: C,71.47; H,7.82; N,2.96.

EXAMPLE 20D

2-Cyclohexylmethyl-1-{2-[3-(2-chlorobenzoyl)phenyl]propyl}piperidine (yellow oil) prepared by oxidation of 15.7 g. (0.036 mole) of 2-cyclohexylmethyl-1-{2-[3-(α-hydroxy-2-chlorobenzyl) phenyl}propyl}• piperidine (described above in Example 3D) in 225 ml. of a solution prepared by dissolving 48 ml. of 50% perchloric acid and 24 ml. of concentrated nitric acid in 240 ml. of 1,2-dimethoxyethane. There was thus obtained 6.4 g. of product.

Anal. Calcd. for $C_{28}N_{36}ClNO$: C,76.77; H,8.28; N,3.20. Found: C,76.47; H, 8.58; N,3.09.

EXAMPLE 21

A solution of 11.0 g. (0.126 mole) of morpholine in 24 ml. of dimethylformamide was stirred with external cooling in a water bath and treated over a ten minute period with a solution of 17.35 g. (0.06 mole) of 1-(3-benzoylphenyl)-1-bromoethane in 24 ml. of dimethylformamide. When addition was complete the mixture was stirred for an additional hour at ambient temperature. The mixture was then filtered, the filter washed with ether, the filtrate poured into 125 ml. of water and the mixture extracted twice with ether. Isolation of the product in the form of the free base from the ether extracts in the conventional manner afforded 14.8 g. of oily product which was chromatographed on alumina using a 1:1 ether:hexane solution as eluent to give 12 g. of 4-[1-(3-benzoylphenyl)ethyl]morpholine as a pale yellow oil.

Anal. Calcd. for $C_{19}H_{21}NO_2$: C,77.26; H,7.17; N,4.74. Found: C,76.95; H,7.11; N,4.61.

EXAMPLE 22

4-{2-[3-(α-Aminobenzyl)phenyl]ethyl}morpholine (15.6 g., 0.05 mole, described in Example 16A) was mixed with 13.8 g. (0.30 mole) of 97% formic acid and 9.4 g. (0.11 mole) of 35% formaldehyde solution. The mixture was heated to 95° C. to effect complete solution of the gummy base, heating was continued for ten hours, and the solution was cooled and poured into a dilute sodium hydroxide/ice mixture. Isolation of the organic material in the usual manner by extraction with ether afforded 15.6 g. of an oil which was chromatographed on 400 g. of alumina using 1.5:98.5 isopropylamine:hexane as eluent. The first ten fractions, 75 ml. each, were collected and set aside, and the next ten fractions, 75-100 ml. each, were combined and taken to dryness to give 10.6 g. of 4-{2-[3-(α-dimethylaminobenzyl)phenyl]ethyl}morpholine as an oil which crystallized on standing, m.p. 60°-63° C.

Anal. Calcd. for $C_{21}H_{28}N_2O$: C,77.74; H,8.70; N,8.63. Found: C,77.20; H,8.60; N,8.48.

EXAMPLE 23

Reaction of the 2-cyclohexylmethyl-1{2-[3-(4-methoxybenzoyl)phenyl]propyl}piperidine described above in Example 7 with hydrobromic acid in glacial acetic acid, and isolation of the product from a neutral medium affords 2-cyclohexylmethyl-1-{2-[3-(4-hydroxybenzoyl)phenyl]propyl}piperidine.

EXAMPLE 24

Reduction of α-(3-bromophenyl)propionaldehyde with sodium borohydride using the procedure described in Example 3 and reaction of the resulting 2-(3-bromophenyl)propanol with an excess of dihydropyran at ambient temperature in the presence of a few drops of concentrated hydrochloric acid affords 2-(3-bromophenyl)propane tetrahydropyranyl ether. Reaction of the latter in diethyl ether with n-butyl lithium followed by reaction of the resulting lithio derivative with benzonitrile using the procedure described in Example 7 affords 2-(3-benzoylphenyl)-propanol which, on reaction with p-toluenesulfonic acid in the presence of pyridine, affords 2-(3-benzoylphenyl)propanol p-toluenesulfonate. Reaction of the latter with 1-cyclohexyl-piperazine in DMF in the presence of anhydrous potassium carbonate affords 1-[2-(3-benzoylphenyl)propyl]-4-cyclohexylpiperazine.

BIOLOGICAL TEST RESULTS

The N-{3-[R$_1$-(phenyl)-C(=X)]-phenyl-lower-alkyl}amines of formulas I and Ia of the invention have been tested in the carrageenin edema (CE) and adjuvant arthritis (AA) tests and found to have anti-inflammatory activity. Data so obtained, stated in terms of percent inhibition at a dose expressed in terms of millimoles (μM)/kg., are given in TABLE A below. For comparative purposes, data obtained in the carrageenin edema test on the reference compound (designated "Ref."), 4-[(3-benzoylphenyl)methyl]morpholine, disclosed in French Pat. No. 1,549,342, are also given. All data were obtained on oral administration.

TABLE A

| Example | Dose | C.E. | A.A. |
|---|---|---|---|
| 1 | 0.005 | 13 | 56** |
|  | 0.02 | 23 | 73** |
|  | 0.08 | 60** | 91** |
|  | 0.324 | 73** | — |
| 1A | 0.004 | 0 | — |
|  | 0.02 | 0 | — |
|  | 0.08 | 51** | — |
|  | 0.324 | 62** | — |
| 1B | 0.004 | 0 | — |
|  | 0.02 | 0 | — |
|  | 0.08 | 13 | — |
|  | 0.324 | Toxic | — |
| 1C | 0.08 | 40* | — |
|  | 0.324 | 77** | — |
| 1D | 0.08 | 36* | — |
|  | 0.324 | 65** | — |
| 3 | 0.005 | 0 | 0 |
|  | 0.02 | 3 | 2 |
|  | 0.08 | 35* | 30 |
| 3A | 0.004 | 0 | — |
|  | 0.02 | 0 | — |
|  | 0.08 | 34** | — |
|  | 0.324 | 75** | — |
| 3B | 0.08 | 19 | — |
|  | 0.16 | — | 91** |
|  | 0.324 | 63** | — |
| 3E | 0.004 | 14 | — |
|  | 0.02 | 34** | — |
| 4 | 0.004 | 0 | — |
|  | 0.02 | 1 | — |
|  | 0.08 | 18 | — |
|  | 0.324 | 72** | — |
| 5 | 0.004 | 14 | — |
|  | 0.005 | — | 64** |
|  | 0.02 | 41* | 70** |
|  | 0.08 | — | 88** |
| 5A | 0.004 | 0 | — |
|  | 0.02 | 0 | — |
|  | 0.08 | 58** | — |
|  | 0.324 | 68** | — |
| 6 | 0.004 | 14 | — |
|  | 0.02 | 5 | — |
|  | 0.08 | 28* | — |
|  | 0.324 | 55** | — |
| 7 | 0.004 | 0 | — |
|  | 0.02 | 22 | — |
|  | 0.08 | — | 63** |
| 7A | 0.08 | 45** | — |
|  | 0.16 | — | 90** |
|  | 0.324 | 60** | — |
| 7B | 0.004 | 3 | — |
|  | 0.005 | — | 61** |
|  | 0.02 | 38* | 55* |
|  | 0.08 | — | 85** |
| 7C | 0.004 | 0 | — |
|  | 0.02 | 10 | — |
|  | 0.08 | 58** | — |
|  | 0.324 | 75** | — |
| 7D | 0.08 | 37** | — |
|  | 0.16 | — | 100** |
|  | 0.324 | 49** | — |
| 7E | 0.08 | 33* | 92** |
|  | 0.324 | 58** | — |
| 7F | 0.08 | 33** | 91** |
|  | 0.16 | — | Toxic |
|  | 0.324 | 51** | — |
| 7G | 0.004 | 33** | — |
|  | 0.02 | 42** | — |
|  | 0.08 | — | 76** |
| 7H(base) | 0.004 | 29* | — |
|  | 0.02 | 44** | — |
|  | 0.08 | — | 81** |
| 7H(HCl) | 0.08 | 68** | — |
|  | 0.324 | 73** | — |
| 7J | 0.08 | 62** | — |
|  | 0.324 | 66** | — |
| 8 | 0.004 | 2 | — |
|  | 0.02 | 21 | — |
|  | 0.08 | 33** | — |
|  | 0.324 | 68** | — |
| 9 | 0.004 | 0 | — |
|  | 0.02 | 0 | — |
|  | 0.08 | 21 | — |
|  | 0.324 | 47** | — |
| 10 | 0.005 | 7 | 25 |
|  | 0.02 | 26* | 63* |
|  | 0.08 | 60** | 91** |
| 11 | 0.004 | 0 | — |
|  | 0.02 | 15 | — |
|  | 0.08 | 29* | — |
|  | 0.324 | 64** | — |
| 12,14 | 0.005 | 21 | 69** |
|  | 0.02 | 41** | 81** |
|  | 0.08 | 51** | 87** |
|  | 0.324 | 69** | — |
| 13 | 0.004 | 0 | 37** |
|  | 0.015 | 15 | 52** |
|  | 0.06 | 37* | 78** |
|  | 0.08 | 54** | — |
|  | 0.324 | 56** | — |
| 15 | 0.004 | 16 | — |
|  | 0.02 | 43** | 92** |
|  | 0.08 | — | 91** |
| 15A | 0.08 | 27 | — |
|  | 0.324 | 29 | — |
| 16 | 0.004 | 16 | — |
|  | 0.005 | — | 80** |
|  | 0.02 | 31* | 89** |
|  | 0.08 | — | 108** |
| 16A | 0.08 | 27 | — |
|  | 0.324 | 39* | — |
| 16B | 0.08 | 0 | — |
|  | 0.324 | 36* | — |
| 16C | 0.08 | 49** | — |
|  | 0.324 | 84** | — |
| 17 | 0.004 | 9 | — |
|  | 0.02 | 16 | — |
|  | 0.08 | 47** | — |
|  | 0.324 | 67** | — |
| 19 | 0.02 | 5 | — |
|  | 0.08 | 0 | — |
|  | 0.16 | — | 1 |
|  | 0.324 | 23* | — |
| 20 | 0.004 | 16 | — |
|  | 0.005 | — | 63** |
|  | 0.02 | 52** | 90** |
|  | 0.08 | — | Toxic |
| 20A | 0.004 | 9 | — |
|  | 0.02 | 25 | — |
|  | 0.08 | 46** | — |
|  | 0.324 | 70** | — |
| 20B | 0.004 | 14 | — |
|  | 0.02 | 0 | — |
|  | 0.08 | 22* | — |
|  | 0.324 | 65** | — |
| 20C | 0.004 | 17* | — |
|  | 0.02 | 15 | — |
|  | 0.08 | 19* | — |
|  | 0.324 | 51** | — |
| 20D | 0.004 | 0 | — |
|  | 0.005 | — | 35* |
|  | 0.02 | 36** | 54* |
|  | 0.08 | — | 79** |

TABLE A-continued

| Example | Dose | C.E. | A.A. |
| --- | --- | --- | --- |
| 21 | 0.08 | 32 | — |
|  | 0.324 | 46** | — |
| 22 | 0.08 | 29 | — |
|  | 0.324 | 63** | — |
| Ref. | 0.08 | 0 | — |
|  | 0.324 | 23* | — |

*Statistically different from controls p. ≦.05
**Statistically different from controls p. ≦.01

Certain of the N-}3-[$R_1$-(phenyl)-C(=X)]-phenyl-lower-alkyl}amines of formula I of the invention have been tested for anti-viral activity against herpes simplex virus types 1 and 2 and have been found to have anti-viral activity. Data so-obtained, expressed in terms of the Minimum Inhibitory Concentration (mcg./ml.), are given in TABLE B below.

TABLE B

| Example | MIC |
| --- | --- |
| 1B | 50 mcg./ml. |
| 5 | 6 mcg./ml. |
| 10 | 6 mcg./ml. |
| 12,14 | 6 mcg./ml. |

I claim:

1. A member of the group consisting of (A) compounds having the formula:

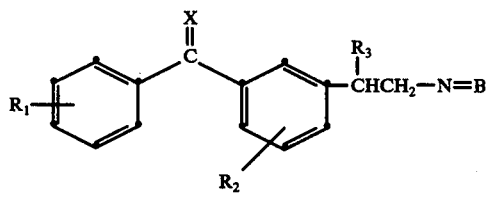

where $R_1$ represents hydrogen or from one to two, the same or different, lower-alkyl, hydroxy, lower-alkoxy, trifluoromethyl, lower-alkylmercapto, lower-alkylsulfinyl, lower-alkylsulfonyl or halogen selected from fluorine, chlorine and bromine; $R_2$ represents hydrogen, or lower-alkoxy or hydroxy in the 4-position, or lower-alkyl in either of the 2-, 4-, 5- or 6-positions; $R_3$ represents hydrogen or lower-alkyl; the group >C=X represents >C=O; and N=B represents the group

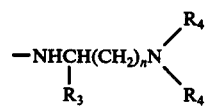

where $R_4$ represents lower-alkyl and (B) acid-addition salts thereof.

2. A compound according to claim 1 having the formula:

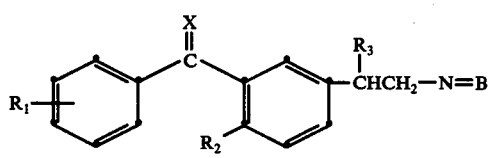

where $R_1$ represents hydrogen, or from one to two, the same or different, lower-alkyl, lower-alkoxy or halogen; $R_2$ represents hydrogen, lower-alkoxy or hydroxy; and N=B represents the group

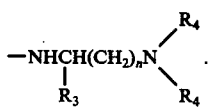

3. A compound according to claim 2 where $R_1$ represents hydrogen or from one to two, the same or different, lower-alkoxy or halogen; and $R_2$ represents hydrogen.

4. N-[2-(3-Benzoylphenyl)ethyl]-N-(3-dimethylaminopropyl)amine according to claim 3.

UNITED STATES PATENT AND TRADEMARK OFFICE
CERTIFICATE OF CORRECTION

PATENT NO. : 4,069,256
DATED : January 17, 1978
INVENTOR(S) : Bernard L. Zenitz

It is certified that error appears in the above-identified patent and that said Letters Patent are hereby corrected as shown below:

Column 1, line 6, reads "continuous-in-part" and should read --continuation-in-part--.

Column 9, line 36, reads "CHO, or (to prepare the compounds......)" and should read --CHO (to prepare the compounds ......)--.

Column 19, line 21 reads "by Van Arman et al., Winter et al.,...." and should read --by Winter et al., Proc. Soc. Exp. Biol. and Med. III, 554 (1962) as modified by Van Arman et al.,...--.

Signed and Sealed this

Twenty-second Day of August 1978

[SEAL]

Attest:

RUTH C. MASON
Attesting Officer

DONALD W. BANNER
Commissioner of Patents and Trademarks